United States Patent
Tolan et al.

(10) Patent No.: US 7,672,858 B2
(45) Date of Patent: Mar. 2, 2010

(54) BEST POSSIBLE PAYMENT EXPECTED FOR HEALTHCARE SERVICES

(75) Inventors: Mary A. Tolan, Burr Ridge, IL (US); Stephen B. Smith, Antioch, IL (US); John T. Staton, Lake Forest, IL (US); Brian J. Rubin, Northbrook, IL (US)

(73) Assignee: Accretive Health, Inc., Chicago, IL (US)

( * ) Notice: Subject to any disclaimer, the term of this patent is extended or adjusted under 35 U.S.C. 154(b) by 504 days.

(21) Appl. No.: 11/789,960

(22) Filed: Apr. 26, 2007

(65) Prior Publication Data

US 2009/0326974 A1    Dec. 31, 2009

(51) Int. Cl.
*G06Q 10/00* (2006.01)
*G06Q 50/00* (2006.01)
*A61B 5/00* (2006.01)
*G06F 19/00* (2006.01)

(52) U.S. Cl. .............................................. 705/2; 705/3
(58) Field of Classification Search ...................... 705/2, 705/3
See application file for complete search history.

(56) References Cited

U.S. PATENT DOCUMENTS

| | | | |
|---|---|---|---|
| 5,235,507 A | 8/1993 | Sackler et al. | |
| 5,819,228 A | 10/1998 | Spiro | |
| 6,061,657 A * | 5/2000 | Whiting-O'Keefe | 705/2 |
| 6,341,265 B1 | 1/2002 | Provost et al. | |
| 2002/0065758 A1 * | 5/2002 | Henley | 705/37 |
| 2002/0123907 A1 | 9/2002 | Strayer | |
| 2005/0033609 A1 | 2/2005 | Yang | |
| 2005/0159980 A1 | 7/2005 | Benja-Athon | |

(Continued)

FOREIGN PATENT DOCUMENTS

| | | |
|---|---|---|
| CA | 2081737 | 5/1993 |
| WO | WO 01/63516 | 8/2001 |
| WO | WO 02/084437 | 10/2002 |

*Primary Examiner*—Gerald J. O'Connor
*Assistant Examiner*—Neha Patel
(74) *Attorney, Agent, or Firm*—John S. Paniaguas; Katten Muchin Rosenman LLP

(57) ABSTRACT

A system is disclosed that is useful by hospitals and other healthcare providers for automatically determining the best possible or maximum amount of payments a healthcare provider can lawfully expect to receive for healthcare resources which takes into account various discounts agreed upon by the healthcare provider with various private insurance companies as well as public (i.e., government) insurance providers, which administer managed healthcare plans including Medicare and Medicaid, all payments received against expected payments and a yield measurement approach for determining the providers performance at a given point in time and across various segments of its operations. In accordance with one aspect of the present invention, contracts between a healthcare provider and all private insurance companies and public insurance providers may be modeled. Various data including healthcare resources provided to patients up to a given point in time, applicable insurance company, and healthcare resource code are entered into the system. The system is able to calculate the best possible revenue that the healthcare provider can lawfully expect to receive taking into account the various discounts negotiated with the various insurance companies. Indeed, once the data is loaded, the system can provide an accurate snapshot of a healthcare provider's best possible expected revenues at any given time based upon services rendered instead of waiting until the healthcare resources have been billed out to insurance companies, patients, and third party payers. It can also provide an accurate snapshot of all payments received against those expected payments to determine yield across various segments of its operations.

6 Claims, 20 Drawing Sheets

U.S. PATENT DOCUMENTS

| | | |
|---|---|---|
| 2005/0273360 A1 | 12/2005 | Drucker et al. |
| 2006/0143050 A1 | 6/2006 | Dean |
| 2006/0167724 A1 | 7/2006 | Petersen, Jr. et al. |
| 2006/0190300 A1 | 8/2006 | Drucker |
| 2006/0247947 A1 | 11/2006 | Suringa |
| 2007/0192146 A1* | 8/2007 | Menocal et al. ............ 705/4 |

* cited by examiner

Overall Flow

Read the Dataload Parameters

Import file path

Database server name

History cutoff date

Default facility code

Process 837s

Process 835s

Create payments from 835?

Create RA records from 835?

Do the ICD9 codes contain period?

Are there decimal points in currency amounts?

Reverse payment sign?

Create CPT4s from detail charges? (always 'N' if 837s is 'Y')

Cross reference

Assign service categories

Delete detail charges (not by post date)

Delete payments (not by post date)

Others

Fig. 4

Sample Cash to Best Possible Scorecard

SAMPLE HOSPITAL
Cash Scorecard

| | 5/31/2005 | 6/30/2005 | FY06 7/31/2005 | FY06 8/31/2006 | |
|---|---|---|---|---|---|
| Calendar Days | 31 | 30 | 31 | 31 | |
| Posting Days (Total for Month) | 21 | 22 | 20 | 23 | |
| GROSS REVENUE | | | | | |
| Month to Date | $ 43,681,010 | $ 44,485,597 | $ 51,435,708 | $ 53,079,246 | (A) |
| BEST POSSIBLE REVENUE | | | | | |
| Month to Date | $ 17,198,968 | $ 19,708,426 | $ 20,683,460 | $ 18,920,406 | (C)<br>(D) - Per Contract Mgmt Tool |
| CASH COLLECTIONS | | | | | |
| Month to Date | $ 18,905,160 | $ 18,010,759 | $ 14,905,695 | $ 20,802,628 | (E) |
| ACCOUNTS RECEIVABLE | | | | | |
| Total AR | 57,895,970 | 58,091,408 | 70,896,609 | 96,043,261 | |
| AR Over 360/365 Days | 1,020,682 | 742,077 | 849,845 | 988,390 | |
| Adjusted AR | 56,815,288 | 56,309,421 | 70,046,860 | 95,054,851 | (F) |
| AR Days (using trailing 90 days Gross Revenue) | 36.93 | 39.28 | 44.56 | 38.59 | (F) / Avg Curr & Prior Mth Gross Revenue Per Day |
| Change in AR Days | (1.50) | (1.65) | 5.28 | (5.96) | |
| Cash Value of AR Day | 531,777 | 598,862 | 602,953 | 654,877 | (G)<br>(K) = (G) / [(A) - (G)] |
| Cash Adj due to Change in A/R Days | (870,078) | (941,301) | 3,765,957 | (3,307,526) | (H) = (G) * (K) |
| CASH PERFORMANCE | | | | | |
| Unadjusted Cash | 107.23% | 97.81% | 72.80% | 103.54% | (E) / Avg of Curr & Prior Month Best Possible (D) |
| Adjusted Cash to Best Possible Revenue % | 102.29% | 92.51% | 92.55% | 80.93% | [(E) + (H)] / Avg of Curr & Prior Month Best Possible (D) |
| Baseline Cash to Best Possible Revenue % | 91.37% | 91.37% | 91.37% | 91.37% | (I) |
| Cash % Variance to baseline | 10.92% | 1.15% | 1.18% | -4.84% | |
| Cash | $ 18,905,160 | $ 18,010,759 | $ 14,905,695 | $ 20,602,528 | (E) |
| Adjusted Cash | $ 18,035,082 | $ 17,069,458 | $ 18,691,652 | $ 17,195,000 | (E) + (H) |
| Cash Baseline | $ 16,110,003 | $ 16,680,346 | $ 16,463,653 | $ 18,093,032 | (J) = Avg Curr & Prior Month Best Possible (D) * Baseline Yield % (I) |
| Overall Cash Improvement/Shortfall - Monthly | $ 2,795,157 | $ 1,150,413 | $ (3,548,087) | $ 2,408,894 | (E) - (J) |
| AR Cash Impact/Clearing Account | (870,078) | (941,301) | 3,765,937 | (3,307,526) | (H) |
| Cash Improvement from Income Statement | 1,925,079 | 209,112 | 237,900 | (898,631) | [(E) + (H)] - (J) |
| Overall Cash Improvement/Shortfall - Contract to Date | 7,342,572 | 8,492,985 | 4,944,929 | 7,353,822 | |
| AR Cash Impact/Clearing Account | (2,724,015) | (3,695,316) | 120,640 | (3,186,865) | |
| Cash Improvement from Income Statement | 4,618,557 | 4,027,669 | 5,065,669 | 4,166,957 | |

Avg Curr & Prior Mth Gross Revenue Per Day = $[(C)_{Curr} + (C)_{Prior}] / [(A)_{Curr} + (A)_{Prior}]$

BEST POSSIBLE PAYMENT EXPECTED FOR HEALTHCARE SERVICES

This application includes a Computer Listing Appendix on compact disc, hereby incorporated by reference.

BACKGROUND OF THE INVENTION

1. Field of the Invention

The present invention relates to a system and method for calculating expected payments and ultimate yield on expected payments for healthcare services and related supplies (collectively and individually referred to herein as "healthcare resources") and more particularly a system useful by hospitals and other healthcare providers for automatically determining the best possible or maximum amount of payments a healthcare provider can lawfully expect to receive for healthcare resources which takes into account various discounts agreed upon by the healthcare provider with various private insurance companies as well as public (i.e., government) insurance providers, which administer managed healthcare plans including Medicare and Medicaid, all payments actually received against expected payments and the ultimate yield leakage on expected payments and source of leakage experienced by the healthcare provider.

2. Description of the Prior Art

Various systems are known in the art for processing payments of healthcare claims. Examples of such systems are disclosed in U.S. Pat. Nos. 5,235,507; 5,819,228; 6,341,265 and US Patent Application Publication Nos. US 2002/0123907 A1; US 2005/0159980 A1; US 2005/0033609 A1; US 2005/0273360 A1; US 2006/0167724 A1; US 2006/0190300 A1 and US 2006/0247947 A1, all hereby incorporated by reference. Systems for processing payments of healthcare claims are also disclosed in International Patent Application Publication Nos. WO 01/63516 A2 and WO 02/084437 A2 as well as Canadian Patent No. CA 2 081 737, also incorporated by reference. Such healthcare payment processing systems are used by insurance companies and government agencies for processing payments to healthcare providers. Examples of systems for processing payments to healthcare providers are disclosed in U.S. Pat. Nos. 5,235,507; 5,819,228; US Patent Application Publication Nos. US 2002/0123907 A1; US 2005/0159980 A1; US 2005/0033609 A1; US 2005/0273360 A1; and US 2006/01900300 A1 and Canadian Patent No. CA 2 081 737. Examples of systems useful by healthcare providers for facilitating payments are disclosed in U.S. Pat. No. 6,341,265; US Patent Application publication No. US 2006/0167724 A1; US 2006/0247947 A1; and International Patent Application Publication Nos. WO 01/63516 A2 WO 02/084437 A2.

In general, the current systems used by healthcare providers provide statements of current charges for all healthcare resources to insurance companies, patients and third party payers. These systems do not provide the healthcare provider with an accurate determination of the revenues that the healthcare provider is entitled to at any given point in time. These systems do not reconcile payments expected and payments received on an account by account basis across all patients. These systems do not compute the yield against expected payments realized by the healthcare provider and do not identify the sources of yield leakage or loss.

In general, payments to healthcare providers by insurance companies and government agencies are based upon agreed upon costs for such healthcare resources. More particularly, most healthcare providers contract with various insurance companies and government agencies to provide healthcare resources to patients subscribing to healthcare plans offered by such private insurance companies and public insurance (i.e., government) providers at agreed upon discount prices. Thus, when patients receive healthcare resources by healthcare providers covered by such plans, the healthcare provider submits a statement to the private insurance company and/or public insurance provider setting forth the resources provided by the healthcare provider and the standard charges for those resources.

In order to facilitate processing of claims for healthcare resources, the American Medical Association (AMA) publishes standardized procedural terminology and associated procedural codes for a myriad of healthcare services including examination, diagnostic, and procedural services. For example, current medical procedure codes are published in "Current Procedural Terminology" $4^{th}$ edition, published by the AMA, hereby incorporated by reference. The procedural terminology and associated diagnostic codes promulgated by the AMA are the most widely accepted medical nomenclature used to report medical procedures and services under public and private health insurance programs. This procedural terminology is also used for administrative management purposes, such as claims processing and developing guidelines for medical care review.

The AMA also publishes codes for medical supplies, also used in processing medical claims. The current codes for medical supplies are published in: "AMA HCPCS 2007 Level II", published by the AMA, hereby incorporated by reference.

The AMA also assigns point values to each procedure and supply code. These point values are used by healthcare providers to negotiate contracts for healthcare services with a private insurance company and/or public insurance provider. More particularly, each procedure and supply code will have an assigned point value. Each healthcare provider negotiates a "conversion factor" for a point value which enables the point values assigned for each procedure code and each supply code to be converted to dollar values.

Healthcare providers typically negotiate contracts with a multitude of private insurance companies and several public insurance providers, which administer managed healthcare plans, including Medicare and Medicaid. Unfortunately, the "conversion factors" in the various contracts negotiated with the insurance companies will differ. Since most healthcare providers bill the insurance companies directly for healthcare resources, it is extremely difficult and cumbersome to determine at any given point in time the maximum amount of payments a healthcare provider can lawfully expect to receive for healthcare resources which takes into account various discounts agreed upon with the various private insurance companies and public insurance providers. Thus, there is a need for a system for accurately and easily determining at any given point in time, the maximum amount of payments a healthcare provider can lawfully expect to receive for healthcare services which takes into account various discounts agreed upon by the healthcare provider with various private insurance and can compare the payments actually received by the provider against the expected payments. There is a further need to understand where any yield leakage is occurring and the sources/causes of the yield loss.

SUMMARY OF THE INVENTION

The present invention relates to a system and method for determining payments for healthcare services and supplies (collectively "healthcare resources") and more particularly a system useful by hospitals and other healthcare providers for automatically determining the best possible or maximum amount of payments a healthcare provider can lawfully expect to receive for healthcare resources which takes into account various discounts agreed upon by the healthcare provider with various private insurance companies as well as public (i.e., government) insurance providers, which administer managed healthcare plans including Medicare and Medicaid, the payments received by the healthcare provider against the expected payments and the yield against the expected payments realized by the healthcare provider. In accordance with one aspect of the present invention, all contracts between a healthcare services provider, and all private insurance companies and public insurance providers may be modeled. Various data including healthcare resources provided to patients up to a given point in time, applicable insurance company and healthcare resource codes are entered into the system. The system is able to calculate the best possible revenue that the healthcare provider can lawfully expect to receive taking into account the various discounts negotiated with the various insurance companies. The best possible revenue can be determined irrespective of whether the healthcare provider has submitted claims to the various insurance companies at the time the determination is made. With the best possible revenue determined, yield against the best possible revenue can be calculated at any point in time. This allows healthcare providers to monitor revenue cycle execution performance and to effectively benchmark performance and effectiveness across facilities, payors, service lines and other criteria.

DESCRIPTION OF THE DRAWING

These and other advantages of the present invention will be readily understood with reference to the following specification and attached drawing wherein:

FIG. 4 is top level diagram of the data flow for the data loader which forms a part of the system illustrated in FIGS. 1-3.

FIG. 6 is an exemplary cash to best possible score card which is an application of the present invention.

DETAILED DESCRIPTION

Figure 1:
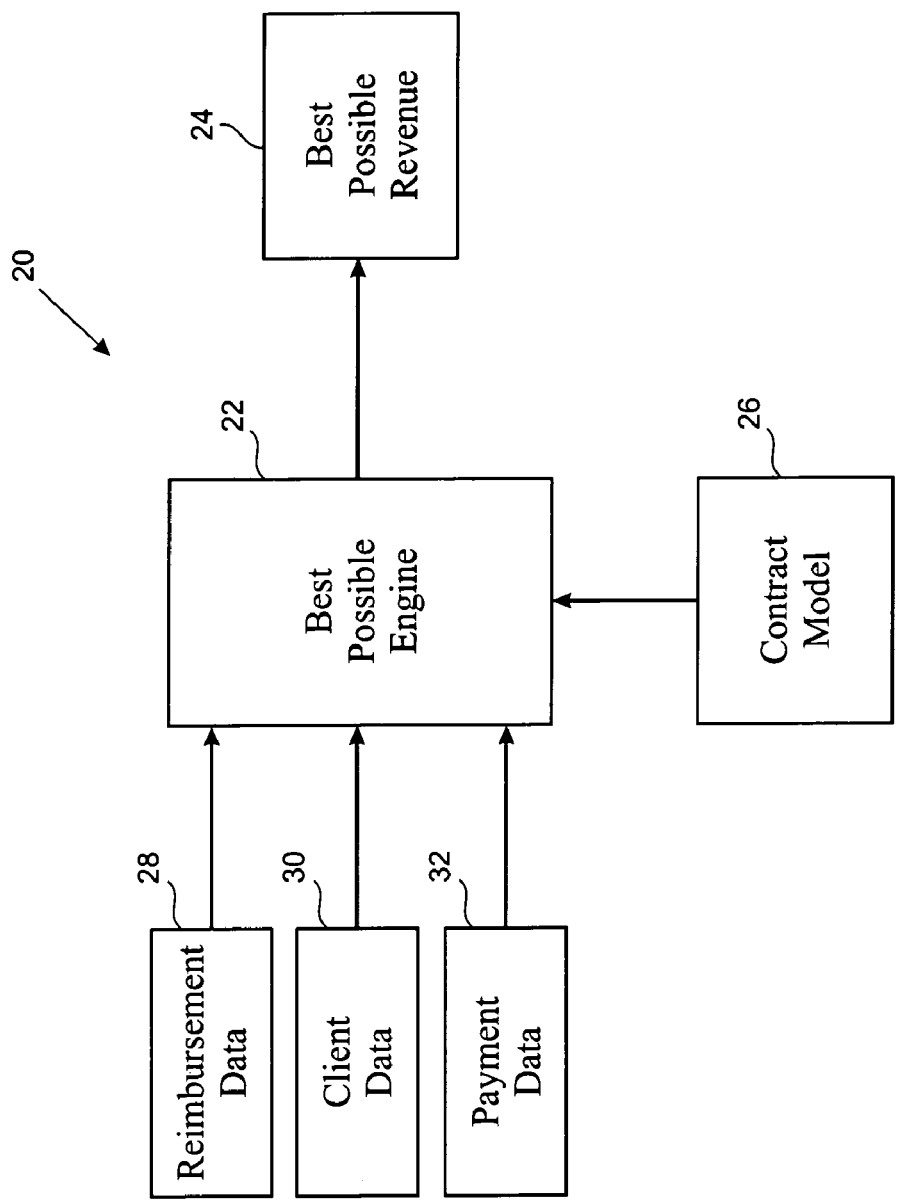
FIG. 1 is a simplified block diagram of a system in accordance with the present invention which can determine at a given point of time the best possible or maximum lawful amount of revenue a healthcare provider can expect.

The present invention relates to a system and method useful by hospitals and other healthcare providers for automatically determining the best possible or maximum amount of payments a healthcare provider can lawfully expect to receive for healthcare resources which takes into account various discounts agreed upon by the healthcare provider with various private insurance companies as well as public (i.e., government) insurance providers, which administer managed healthcare plans including Medicare and Medicaid. In accordance with one aspect of the present invention, all contracts between a healthcare services provider and all private insurance companies and public insurance providers are modeled. Various data including healthcare resources provided to patients up to a given point in time, applicable insurance company and healthcare resource code are entered into the system. The system is able to calculate the best possible revenue that the healthcare provider can lawfully expect to receive taking into account the various discounts negotiated with the various insurance companies. Indeed, at any given time, the system can provide an accurate snapshot of a healthcare provider's best possible expected revenues based upon services rendered, the payments actually received by the healthcare provider against the expected payments and the yield against those expected payments realized by the healthcare provider.

There are various benefits in providing a healthcare provider with a snapshot of its maximum collectible revenue and its success at collecting that maximum collectible revenue, at a given point in time and in providing the healthcare provider analytical insight into those aspects of its services for which it is not being paid what it is due. Most importantly, this information can be used as a strategic tool by a healthcare provider to measure and improve its revenue yield, for example, by facility, payer, service line and patient type. More particularly, the system in accordance with the present invention identifies claim and payment history including denials by various payers including insurance companies, which can be used by a healthcare provider to improve their contract position with an insurance company. The system can also be used to identify underpayments at the time of adjudication which can be used to speed resolution of such underpayments. The system is also able to accurately measure shifts in selfpay and insured patient residuals (i.e patient co-pays). These shifts can have a significant impact on the cash flow of a healthcare provider. By identifying these shifts early, measures can be taken to compensate for these shifts.

The industry currently measures performance in a variety of ways, the most prevalent being accounts receivables days and trends in cash collections. Those organizations (and most consulting firms) that do attempt to measure net revenue collection performance utilize either a Net Revenue to Gross Revenue Ratio or Cash to Gross Revenue Ratio. However this measurement approach is flawed as it does not normalize for payer mix shifts and contracted reimbursement changes and, as a result, management cannot isolate and gauge the impact of its actions on actual results. In addition, this current industry measurement approach trends downward over time, due to the impact of gross revenue price increases that exceed net revenue increases. Actual comparisons of net revenue or cash collections suffer from the same flaws.

These measures are very imprecise and are not easily understood in the context of changes in volume, payer mix, service line (i.e., cardiology, oncology, etc.) and do not allow management to understand causality of fluctuations, e.g. what is due to revenue cycle execution vs. contract, volumes, service mix. This also means that relative benchmarking is problematic.

The methodology described herein solves the problems mentioned above and can be used to calculate net revenue yield. Net Revenue Yield=Adjusted Cash Collections/Best Possible Compliant Net Revenue. An exemplary cash scorecard for best possible compliant net revenue for a healthcare provider is illustrated in FIG. 6.

The first step of this process is to calculate the Best Possible Compliant Revenue. In general, this is done by modeling the payment terms of each payer and running the actual gross revenue for every episode of care through the model assuming no denials and underpayments. The model also assumes 100% collection of co-insurance and deductibles. For self-pay patients, the system determines the amount after application of a self-pay and/or charity discount.

The second step is to calculate the Adjusted Cash Collections. A cash adjustment is required based on the fact that cash collections during any period, including a baseline comparative period, are impacted by changes in accounts receivable (AR) levels. There are two methods for calculating the impact of changes in accounts receivable—the direct method and the indirect method. The direct method is used when patient AR has been adjusted to its specific contract value (at an account level) based on the specific contract terms applicable to that account. The indirect method is used when AR is recorded at its gross charge value, and patient accounts have not been adjusted to their specific contract value. An example of each follows:

Direct Method

In this method, the cash adjustment may be calculated by taking the change in net AR less than 365 days old from the previous period to the current period.

For example:

| | |
|---|---|
| Cash collections for the period | $14,413,906 |
| Net AR at the beginning of the period | $19,597,995 |
| Net AR at the end of the period | $19,071,027 |
| Cash from the reduction of Net AR | $(526,968) |
| Adjusted cash collections for the period | $13,886,938 |

Indirect Method

In this method, the cash adjustment may be calculated by first calculating the total gross AR days change for the period (changes in the days in gross receivables over 365 days old are eliminated from the calculation). Next, the total cash collected for the period is divided by the number of days in the period plus or minus the AR day change to determine the Cash Value of an AR Day. Subsequently, the days reduction is multiplied by the Cash Value of an AR Day to determine the total cash value of the AR increase/decrease for the period.

For example, assume the following:
Cash collections in period were $14,413,906
Cash value of an AR day (Cash collections/# of days in the period)=$435,511
Days in AR period decreased from 65.50 to 64.29 or 1.21 days in the period
Cash value of an AR day of $435,511* 1.21 days=$526,968 of Cash from AR reduction

| | |
|---|---|
| Cash Collections | $14,413,906 |
| Cash from AR Reduction | (526,968) |
| Adjusted Cash Collections | $13,886,938 |

After the Adjusted Cash Collections are calculated, the Net Revenue Yield and Improvement in Yield can be determined in step three. More particularly, the Net Revenue Yield can be calculated as mentioned above for a prior comparative period and a measurement period to measure improvements. The prior comparative period is flexible and selected by the user. The improved Net Revenue Yield (NRY) is calculated as follows:

Measurement Period NRY-Baseline NRY=Improved Yield*Best Possible Compliant Revenue=Net Revenue Yield Improvement For example, assuming:
Measurement Period Net Revenue Yield=86.70%
Baseline Net Revenue Yield=83.30%
Measurement Period Best Possible Compliant Revenue $18,195,069 Improved Net Revenue=(86.70%-83.80%)*($18,195,069)=$618,632

Best Possible Compliant Revenue

Figure 2:
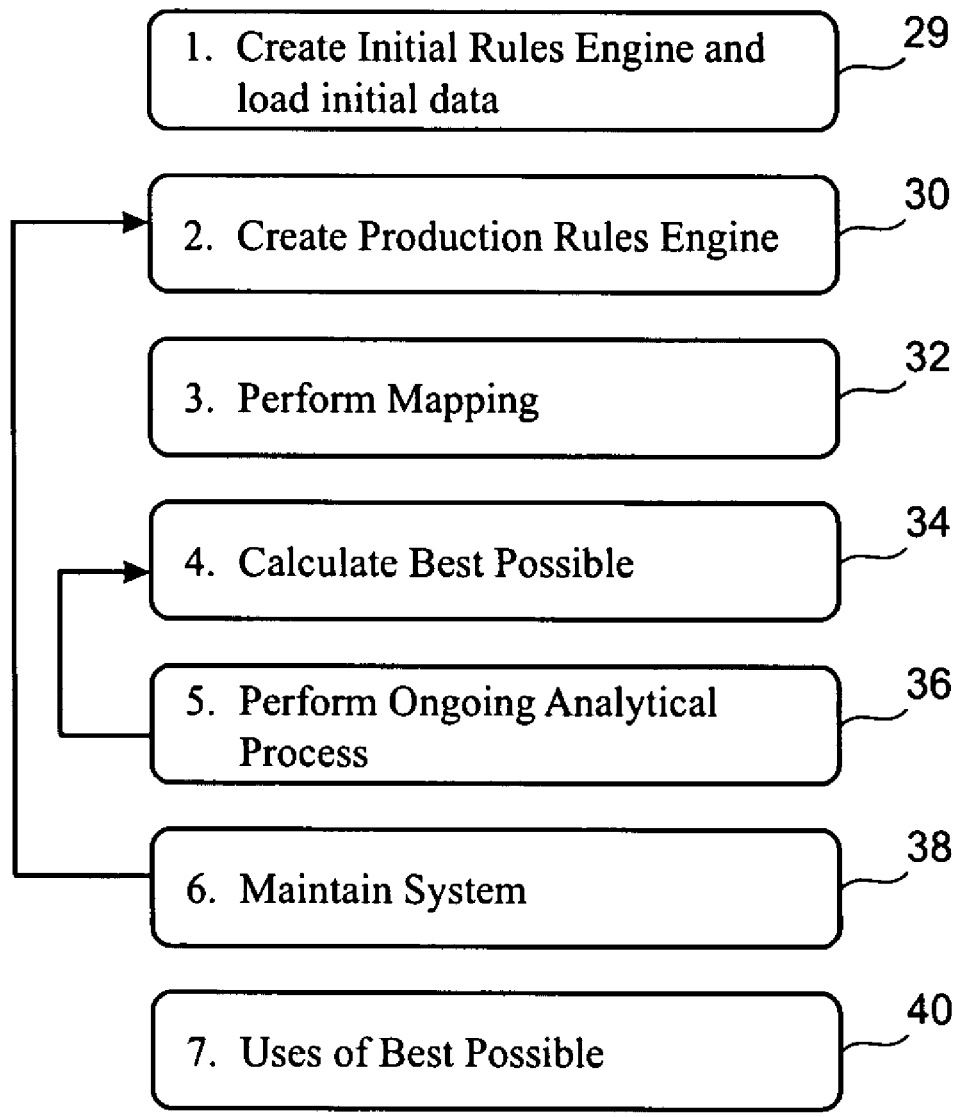
FIG. 2 is a top level flow diagram for the system in accordance with the present invention.

FIGS. 1-3 represent a flow chart for the system in accordance with the present invention for determining the best possible revenue that a healthcare provider can lawfully expect at a given point in time. The system includes a data loader for loading various patient data and a rules engine which controls the loading of the data on a patient account basis. As used herein, patient accounts are defined as patient visits from the time of initial patient registration on admission to the time of patient dismissal or discharge. Once all of the data is properly processed, as discussed in detail below, the best possible revenue can be determined for a given point of time. FIGS. 4-5G are lower level logic diagrams illustrating the data loading process. FIG. 6 is an exemplary cash to best possible score card, which is an application of the present invention.

FIG. 1 is a simplified flow diagram of the system, generally identified with the reference numeral 20. The system 20 includes a calculation engine 22 for determining the best possible revenue 24, one or more contract models 26 as well as raw total charge data 28, patient data 30, and payment data 32.

As mentioned above, healthcare providers negotiate with insurance companies to determine the discount that will be applied for healthcare resources provided to beneficiaries of the insurance company. Since each insurance company will likely have a different discount that has been negotiated by the healthcare provider and memorialized in a contract, each contract that a healthcare provider enters into with an insurance company is modeled as indicated by the block 26. As mentioned above, the payment terms of each payer in effect in the baseline period are modeled assuming zero denials and zero underpayments. These contract models are fed into the processing engine 22.

Various data is fed into the processing engine 22 in order to calculate the best possible revenue. Raw total charge data 28 provides the equivalent of the undiscounted cost for the healthcare resources provided to the patients mentioned below. This raw total charge data 28 may be in the form of the "CPT4" codes discussed above. The patient data 30 identifies the patient demographic information, patient payer information and healthcare resources received. The payment data 32 includes payment data from all resources including insurance companies, selfpay residuals, and third party payers. The processing engine 22 applies the proper discount and calculates the maximum possible revenue that the healthcare provider can lawfully expect for a given time period based upon services rendered and irrespective of whether the healthcare resources have been billed.

Best Possible Flow Chart

FIG. 2 is a top level flow diagram of the system for calculating the best possible revenue in accordance with the present invention. FIGS. 3A-3I are more detailed flow charts of the system illustrated in FIG. 2. Referring first to FIG. 2, a rules engine is created in step 29 and initial data is loaded. The rules engine is based on contract modeling as discussed above. Loading of initial data includes various diagnostic, procedure, and supply codes as well as raw patient data. During step 29, any new contracts or contract changes are also modeled into the system. Additionally updated codes, for example, diagnostic and procedure codes are loaded into the system.

In step 30, a production rules engine is created. This production rules engine is based in part upon minor changes to the initial rules engine based upon the content of the data being fed into the system. As discussed in more detail below, the production rules engine compensates for the fact that healthcare providers maintain patient visit data in a slightly different manner. The production rules engine is specific to each healthcare provider and allows the system to be used by different healthcare providers despite these differences and determines whether a visit is part of an existing claim or a new claim.

In step 32, all patient data 30 in the form of patient accounts is mapped to a specific contract model. Once all of the data is loaded, the system in accordance with the present invention is able to calculate in step 34, on a per patient account level, the best possible revenue the healthcare provider can expect from all payers legally required to pay on an account, such as an insurance company at a given point in time. The system can also be used to model selfpay and charity discounts. The aggregate of all the best possible revenues for all of the patient accounts thus provides a healthcare provider with a snapshot of the maximum revenue a healthcare provider can expect based upon services rendered. As will be discussed in more detail below, the system also incorporates payment data from all sources to provide a snapshot of the maximum net revenue due at a point in time.

In order to account for changes in contracts over time, the system users can perform an on-going analytical process in step 36. This process takes into account changes in contracts, for various reasons. For example, new employers may come into an area which insures its employees with an insurance company that has not been previously modeled in the system. Similarly existing employers in the area change to a new insurance company not currently modeled in the system. In particular, new contracts and changes to existing contracts are modeled so that new client data is mapped to the proper contract.

In order to keep up with latest changes in the market, the system updates the Global Tables in step 38. These updates may include updating the Raw Data 28 (FIG. 1) to take into account new codes, such as CMS, Medicare/Medicaid codes, being released. In particular, various known diagnosis and procedure codes are known to be updated at least once a year. Public payer codes, such as Medicare codes, are known to be updated more frequently, such as, on a quarterly basis. These codes are periodically updated in the Global Tables to account for the various changes.

As will be discussed in more detail below, the system can provide various reports that can be used by a healthcare provider to more effectively manage cash flow. These reports are identified in FIG. 2 with the reference numeral 40.

Figure 3A:
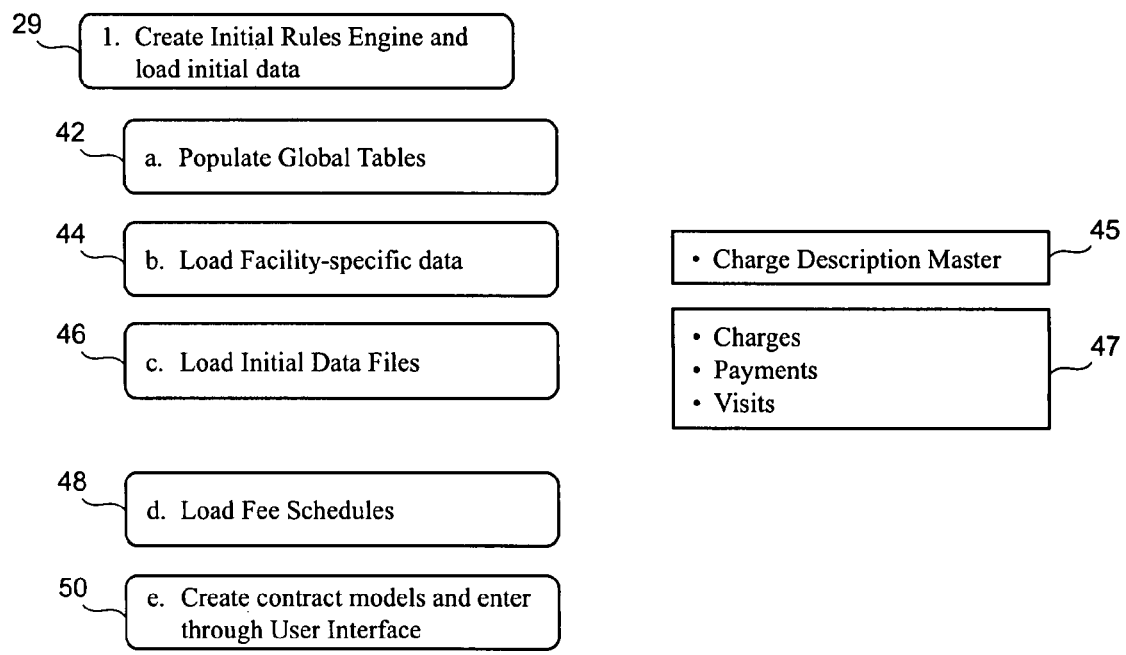
FIGS. 3A-3I are lower flow level diagrams of the system illustrated in FIG. 2.

As mentioned above, FIGS. 3A-3I are more detailed flow charts of the system and method illustrated in FIG. 2. In particular, FIG. 3A illustrates step 29, which relates to creating an initial rules engine and loading initial data, as illustrated in FIG. 2 and discussed above, in more detail. Referring now to FIG. 3A, the step of creating an initial rules engine and loading initial data is comprised of steps 42-50. Initially in step 42, Global Tables are populated. In other words, data from various sources is uploaded into the Global Tables. More particularly, these Global Tables may include various categories of data available from various sources including: Admission Type, Admission Source, CPT Codes, Discharge Status, Discrepancy Codes, Hospital Process Codes, ICD-9 Diagnosis Codes, ICD-9 Procedure Codes, Physician Roles, Physician specialties, Reason Codes, Standard DRGs, Standard RUGs, Standard Patient Types, Standard UB-92 Codes, User Defined Fields as well as others.

The Code type data is uploaded from various code content providers, such as the American Medical Association, the US Department of Health and Human Services for Medicare/Medicaid codes, and others. Non-specific patient data, such as the Admission Type, Admission Source, Discharge Status, etc, may also be input into the system by the healthcare provider.

The Global Tables are collections of data, which are the same for all facilities. These tables contain standardized sets of data, used by the system when building Fee Schedules, discussed below. These Global Tables can also be viewed and printed for reference purposes.

Initial data loading also includes loading facility specific data into Facility Reference Tables, as illustrated by the box 44. These Facility Reference Tables are collections of data that are unique for specific facilities. These tables contain sets of data that are used by the system when building Fee Schedules and Contracts. They may also be viewed and printed for reference purposes. For example, the Facilities Reference Table may include a Charge Master (CDM), which is a list of each and every charge code available at a specific facility along with a description, as indicated by box 45.

In addition to populating the Global Tables and Loading the Facility Reference Tables, patient data files are loaded, as indicated by the box 46, as part of the initial data load. As indicated by the box 47, these patient data files include, for example, patient demographic data, payment data, raw charge data, and patient visit data. The payment data may include the payment amount, identity of the payer, i.e., Blue Cross Blue Shield, Medicare, etc. and may also include the specific plan, i.e., HMO, PPO, etc under which payment was paid.

The initial data load includes loading of fee schedules, as indicated by the box 48. The fee schedules are driven by the contracts. The Fee Schedules allow the user to build a list of Codes and associate a specific Rate with each Code. The nature of the Code depends on the Fee Schedule Type that is being built. For example: A UB-92 Fee Schedule of MRI's will contain UB-92 Codes 610-619 and their associated rates. The rates can be Case Rate, Per Unit Rate, or Percent of Charges.

In addition to loading data as discussed above, the system also creates an initial Rules Engine. The Rules Engine is based upon the various contracts negotiated by the healthcare provider. Basically, each and every contract negotiated by a healthcare provider is modeled in terms of a payer and the contract reimbursement terms with each payer. The contract reimbursement terms are found in the physical contracts the healthcare provider has with the various public and private insurance companies. Selfpay and charity discounts can also be modeled. These contract reimbursement terms can be based upon per diem, CPT4 Codes, ICD-9 Codes, etc.

Figure 3B:
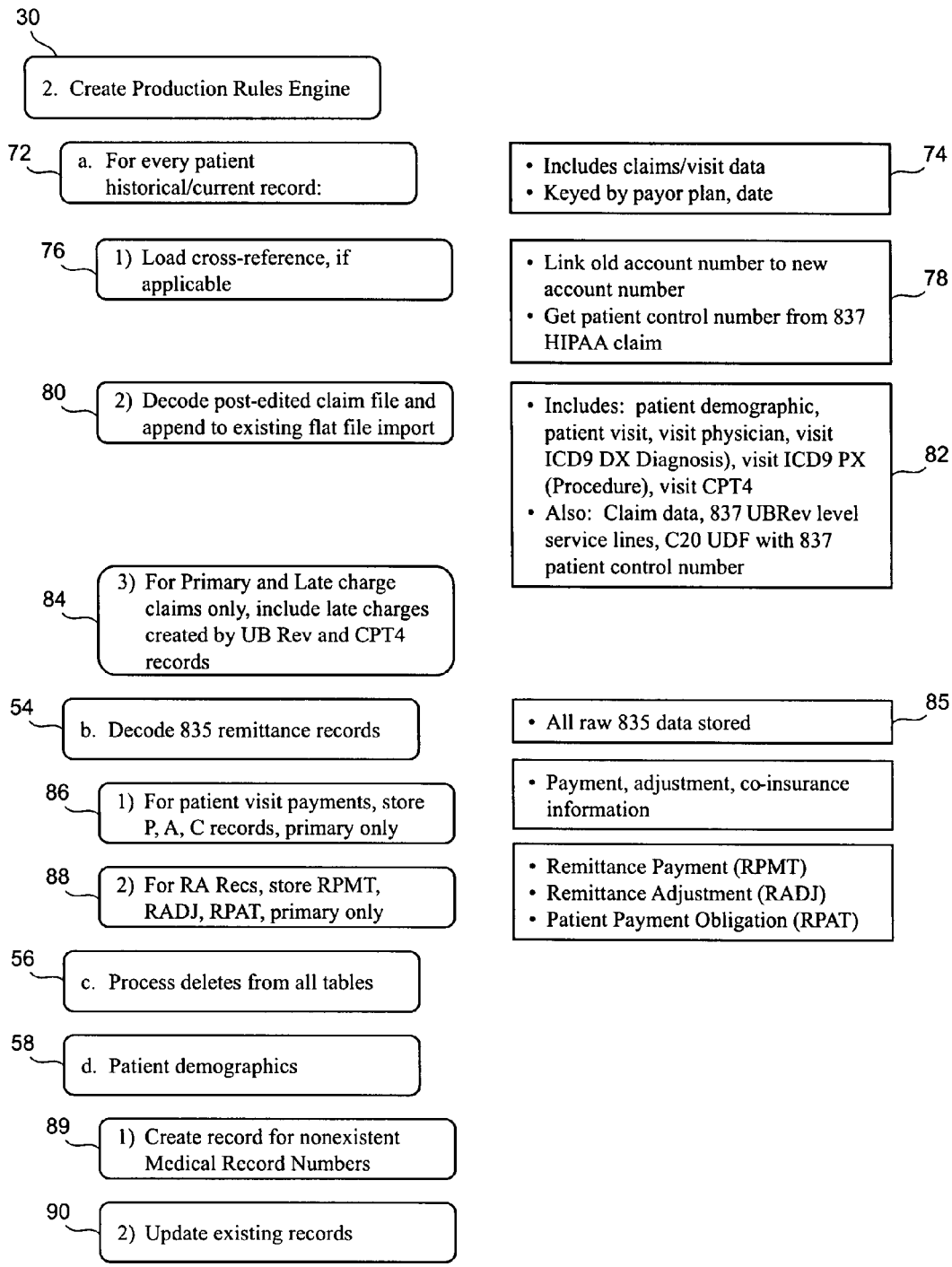

Referring to FIG. 3B, after the initial data is loaded and the initial rules engine is created, a production rules engine is created, as indicated by the box 30. As mentioned above, the production rules engine is specific to each healthcare provider and is used to enable the system to take in data in different formats for each healthcare provider and convert it to a universal format useable by the system. For example, some healthcare providers create a new account number for each visit by the same patient. Thus, if a patient had, for example, 10 different visits with a particular healthcare provider, the patient would be covered under 10 different account numbers. Yet other healthcare providers provide each patient with a single account number. The production rules engine allows the system to be used by different healthcare providers despite these differences and determine whether a visit is part of an existing claim or a new claim.

Figure 3C:
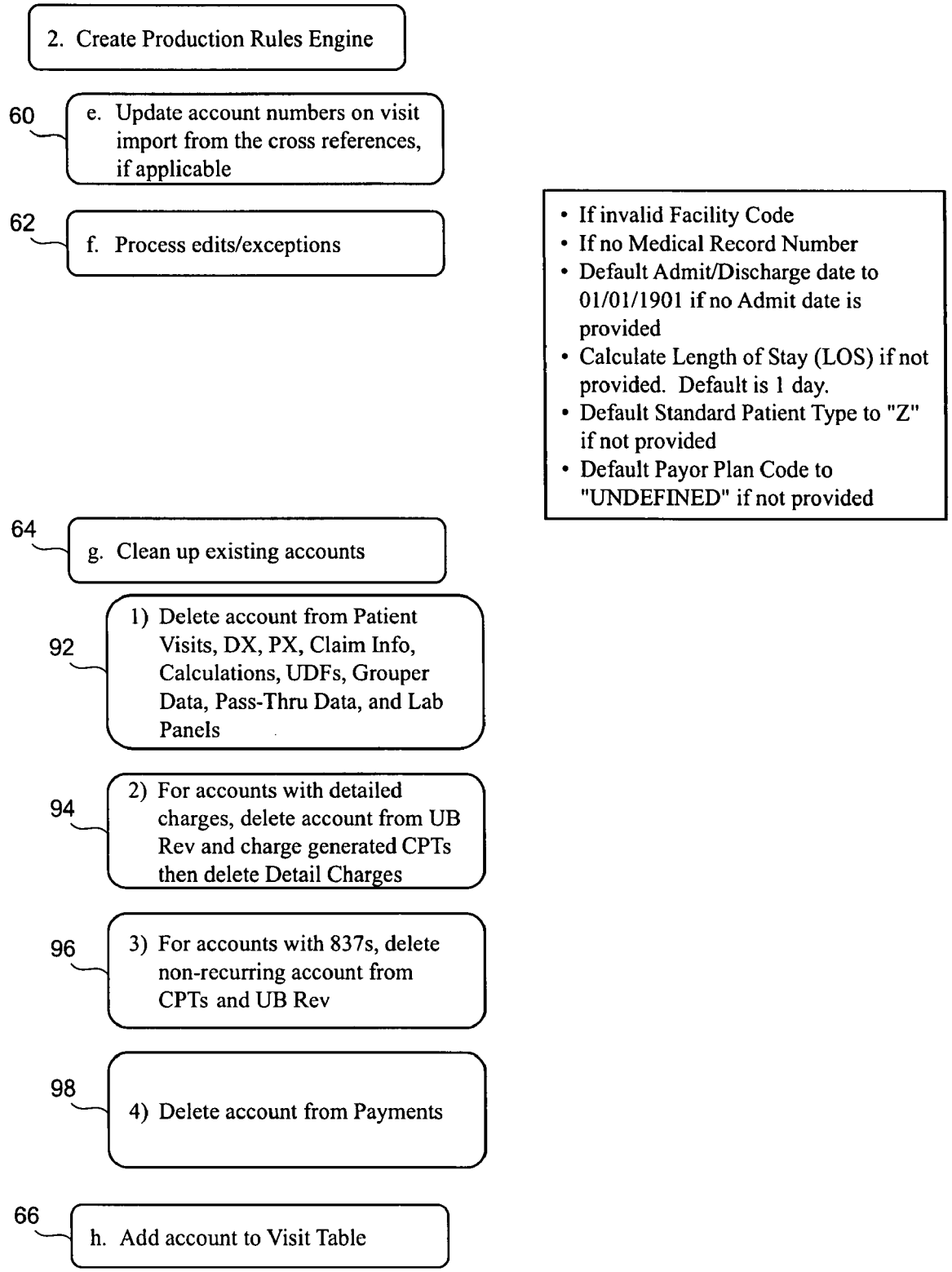
Figure 3D:
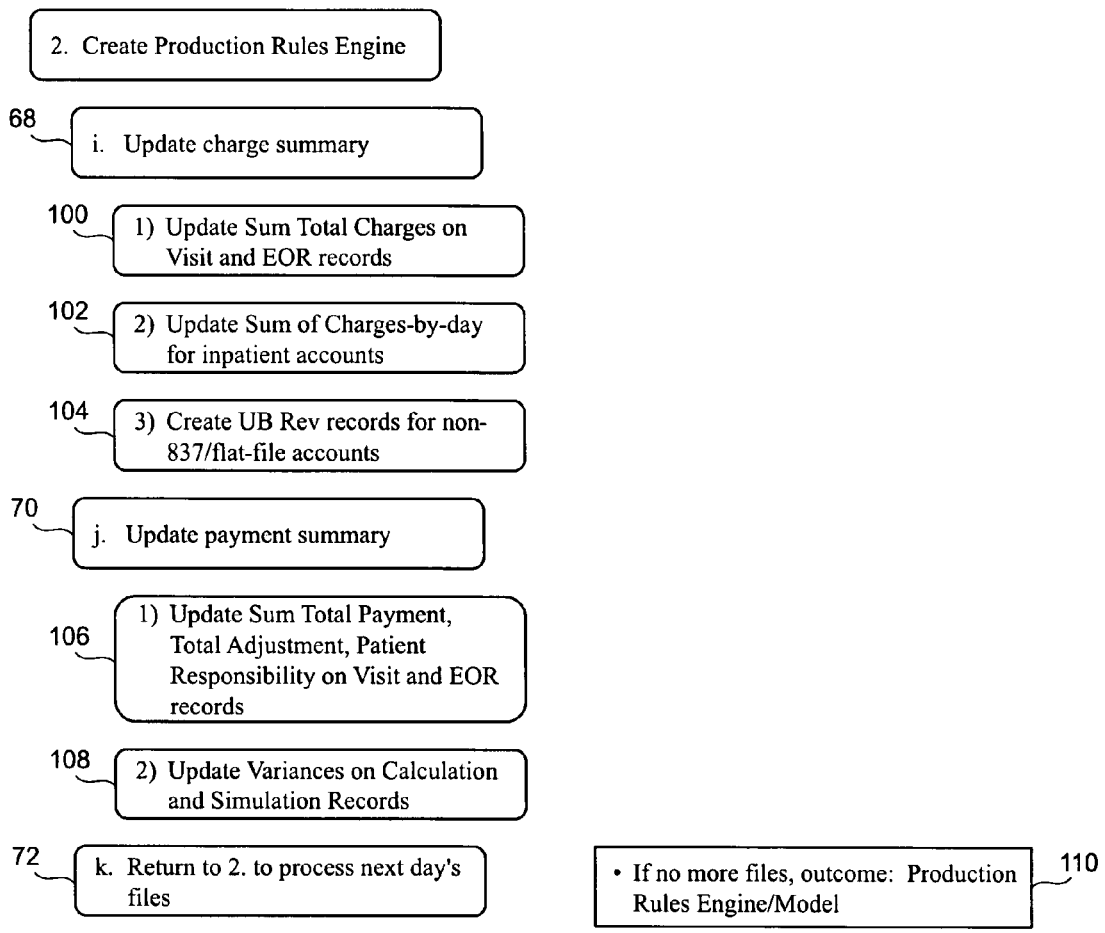

There are various aspects involved in creating a production rules engine, as indicated by the boxes 52-72, illustrated in FIGS. 3B-3D. Referring first to FIG. 3D, as indicated by the box 52, the system checks every patient historical or current record. More particularly, patient records are initially created during the patient registration process. While the patient is within a healthcare facility, various charges for procedures and supplies are input into the system by various medical personnel and stored in the patient record. Upon dismissal of the patient, the charges are summarized and sent to the billing department. The billing and/or medical records department codes in all procedure codes in accordance with notes from the attending physician or other healthcare provider defining a post-edited claim file that is ready to be sent to a payer. As indicated by the box 74, the patient records include all claim and visit data keyed by payer plan and date.

As indicated by the box 76, account number cross references are loaded for each patient record, if applicable. For healthcare providers that use claim numbers rather than account numbers when filing insurance claims for each patient visit, the claim numbers are linked to the account numbers, as indicated by the box 78. In addition, patient control numbers are extracted from the 837 HIPAA claim forms created by the billing department that are used to submit a claim to a healthcare provider. As indicated by the box 80, the post-edited claim file is decoded. The post-edited claim file is normally in the format of a HIPAA 837 claim form, which, as mentioned above, is used by healthcare providers to submit claims for payment to private insurance companies as well as for patients covered by Medicare or Medicaid. These post-edited claim files are appended to "flat" files used for selfpay, charity, and any other non-837 claims. As indicated by the box 82, these files are decoded and include various data including: patient demographic data as well as the codes for the various services received by the patient including codes for: patient visit, visit physician, visit ICD9 DX (Diagnosis), visit ICD9 PX (Procedure) and visit CPT4 data. The patient records may also include claim data, 837 UBRev (UB Revenue Code) level service lines, and/or C20 UDF (User Defined Field named C20) with 837 patient control number. At this stage, all of the patient records irrespective of the payer are assimilated in order to create current list of charges for all patient records. In particular, the list includes charges or revenue, as available from the HIPAA 837 forms for claims covered by private and public insurance companies, as well as a list of charges or revenue available from "flat" files for selfpay, charity, and all non-837 claims.

Late charges are also part of the maximum or best possible revenue at any point in time. As such, as indicated by the box 84, late charges are added to the list of charges or revenue mentioned above. At this point, a current list of charges or revenue due from all sources is available less any payments or remittances from all sources.

As indicated by box 54, raw payment data, as illustrated by the box 84, is extracted for all payments made by payers using HIPAA 835 Remittance Forms. For each patient visit, payment, adjustment and co-insurance information for the insured's primary insurer is stored, as indicated by the box 86. The foregoing information relates to payments actually received. The system also takes into account remittance advice records (RA Recs), which relates to payments to be made. These remittance advice (RA) records are messages on a HIPAA 835 form on a line item level for each claim, which identifies the payment status of each item on a claim. These remittance advice messages enable a healthcare provider to determine the portion of a claim that will be paid by the payer and normally fall into one of the following categories: remittance payment (RPMT), remittance adjustment (RADJ) and remittance payment obligation (RPAT).

The system then deletes information regarding patient visits and related visit data including UB Rev, CPT4, Physician information, etc. for those visits requiring deletion per the Delete Accounts list per box 56.

The system also maintains patient demographic information, e.g., name, current address, and medical record number, as indicated by the box 58. For patients without medical record numbers, a medical record number is created, as indicated by the box 88. In addition, any changes to patient demographic information, for example, input into the system during patient registration, is updated in step 90.

As mentioned above, for each patient visit, data is input into the system from the time of patient registration to patient dismissal and post-visit editing. Assuming a new account number is assigned at registration, the account numbers are updated on the patient visit records, as indicated by the box 60. The patient visit records identify all patient visits by all patients.

In order to account for missing or incorrect information, the system creates an exceptions report, as indicated by the box 62. There are various situations that can cause an account to land on the exception report. These situations may include:
Invalid facility code.
No medical record number.
Default Admit/Discharge date to Jan. 1, 1901 if none provided.
Calculates length of stay if no length of stay provided. Length of stay default is 1 day.
Default patient type to "Z" if none provided on flat file.
Default Payor Plan Code to UNDEFINED if not provided.

As indicated by the box 62, these exceptions and defaults are processed. In particular, those accounts appearing on the exception report are reviewed. The missing information that caused the account to appear on the exceptions report is asssessed by the healthcare provider and can be resent to the system.

For all updated information, it is necessary to clean up existing accounts by first removing the existing information, as indicated by the box 64. For example, for data that has already been processed by the rules engine and thus included in the calculation of the best possible revenue, this data must be removed from the calculation since the data is probably not valid anymore. As such, as indicated by the box 92, the visit data is deleted from patient visits, diagnosis codes (DX), procedure codes (PX), claim specific data, calculations, user defined fields (UDFs), Grouper data (i.e., government data), pass-thru data and lab panels (i.e., outpatient labs). For accounts with detailed charges (i.e., selfpay accounts), the account is deleted from UBRev and charges from CPTs are deleted as well as detail charges being moved back to the hold, as indicated by the box 94. For accounts with HIPAA 837 form data available, the non-recurring account is deleted from the CPTs and UBRev, as indicated by the box 96. Finally, the payments are moved back to the hold, as indicated by the box 98. After the existing accounts are cleaned up, the new account is added to the visit table, as indicated by the box 66.

After the existing accounts are cleaned up, the charge summary is updated, as indicated by the box 68. The charge summary is updated for both insured patients for whom a HIPAA form 837 exists as well as "flat" file patients. As indicated by the box 100, the sum total charges are updated for the visit as well as the Explanation of Reimbursement (EOR) Records. The EOR records provide detailed breakdowns for the expected reimbursements. For payers that pay based upon thresholds, the sum of charges by day for in-patient accounts is updated, as indicated by the box 102. For self-pay patients visits for which no HIPAA form 837 exists, the system goes through the detailed charges for the patient, available in the patient visits table, and creates a pseudo UBRev record, available on HIPAA 837 forms, as indicated by the box 104.

As indicated by the box 70, the payments from all sources are summarized. In particular, as indicated in box 106, the Sum Total Payment, Total Adjustment and Patient Responsibility fields per visit are updated on each Patient Visit record, as indicated by the box 106. In addition, the Variance between actual payments versus expected reimbursement is updated for the actual Explanation of Reimbursement records and simulation Explanation of Reimbursement records. These payments are all summarized, i.e tabulated, at the visit level. In order to keep track of expected payments as opposed to payments received, the system tracks variances, as indicated by the box 108. These variances relate to the accounts that are not paid in full. For example, assume $100 is due for an account and a payment of $30 is received. In this example, the variance is $70-the unpaid amount of the claim. Rather than recalculate the amount due on a claim, the system stores variances on each Visit.

The above described system is used to load and process data. As mentioned above, a patient account is created during patient registration. During a patient's stay, various data is entered into the account by various personnel at the healthcare provider facility. This data includes diagnostic codes (DX), procedure codes (PX) and various supply codes. Data may be continuously entered into a patient account until the patient is dismissed, except for limited post-editing of an account, as discussed above. In addition, new patient records can be expected to be created every day due to new patient admissions. Rather than recalculate the best possible revenue every time a new patient record is entered, the system can be configured to process the new patient records on a periodic basis, for example, as indicated by the box 72. If there are no new patient records to process, the production rules engine is complete, as indicated by the box 110.

Figure 3E:
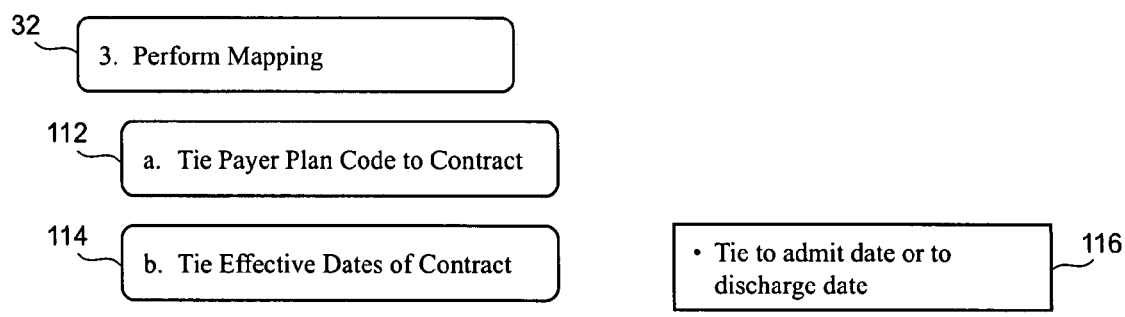

In addition to loading the raw charge data 28, patient data 30 and the payment data 32, as shown in FIG. 1, all patient accounts are mapped to a specific contract model, as indicated by the box 32 (FIGS. 2, 3e). As mentioned above, the contract models identify the reimbursement terms of each public and private insurance payer. Accordingly, as indicated by the box 112, the payer plan codes identified during the registration process by the patient are mapped to a modeled contract. The effective dates of the contract are reviewed as well, as indicated by the box 114. These effective dates can be linked to the admit date or discharge date, as indicated by the box 116.

Figure 3F:
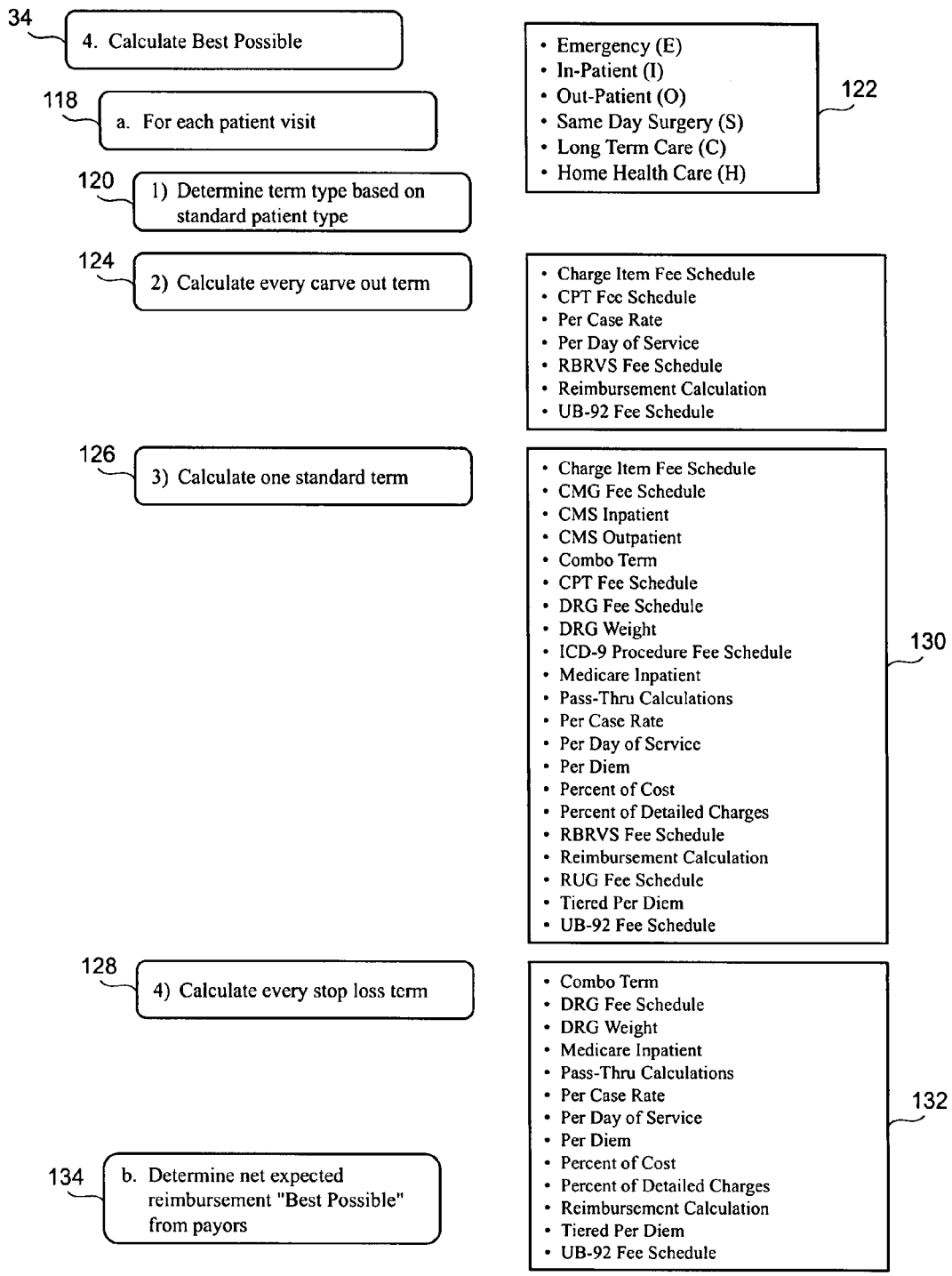

Referring to FIG. 3F, once the data is loaded in accordance with the rules of the production rules engine, the best possible revenue can be calculated, as indicated by the box 34. Various calculations are made for each patient visit based on the Standard Patient Type and the admit date OR discharge date on the visit, as indicated by the box 118. The standard patient types, as indicated by the box 120, determines which terms are used for calculations. Examples of patient types indicated in box 122 include emergency (E), in-patient (I), out-patient (O), same day surgery (S), long term care (L) and home healthcare (H). Additionally, the system is configured with three term types which can be placed under the appropriate Standard Patient Type. Each Standard Patient Type modeled can have Carve Out Terms, Standard Terms, and Stop Loss Terms.

All Carve out terms are calculated for each patient visit, as indicated by the box 124. The carve out terms are based upon the negotiated contracts with the payers which were modeled and loaded initially. The contracts can have any number of carve out terms or no carve out terms at all. In particular, a claim for a full day at a hospital may include a myriad of detailed charges for various procedures and supplies. Thus, the system first determines the carve outs for each patient visit. These carve out terms are part of the contract models discussed above and can be based on fee schedules. See box next to box 124 for a list of Carve Out Term types.

After the carve out terms are processed and the revenue determined for those terms, the system processes one standard term for each visit, which will include processing of any charges not carved out, as indicated by the box 126. Various exemplary standard term types are indicated in the box 130 on FIG. 3F. These terms are negotiated by the healthcare providers with the various payers and also include terms for discounts for selfpay and charity patients that were previously mapped to the patient accounts, as indicated in the boxes 32, 112 and 114 (FIG. 3E).

Next, all the stop loss terms are processed, as indicated by the box 128. These stop loss terms may relate to the maximum amount a payer will pay for a patient visit. Exemplary stop loss terms are indicated in the box 132 (FIG. 3F). These stop loss terms are part of the contract models discussed above.

As mentioned above, the terms used—carve out terms, standard terms, and stop loss terms are determined on a per patient visit level. Since each patient visit is normally assigned a new patient account number, the best possible revenue can be determined on an account level for all accounts at a given point in time, as indicated by the box 134. The best possible revenue determination for the individual accounts can be used for various purposes, as discussed below, and can be aggregated together to provide the best possible revenue available from all patient accounts. The calculation of the best possible revenue on a per account basis is automatically determined and takes into account the specific discounts negotiated with the payer that is responsible for some form of payment of the patient account. It also takes into account any special contract terms, such as carve out and stop loss terms to provide a relatively accurate calculation of the best possible revenue from the patient accounts currently in the system.

Figure 3G:
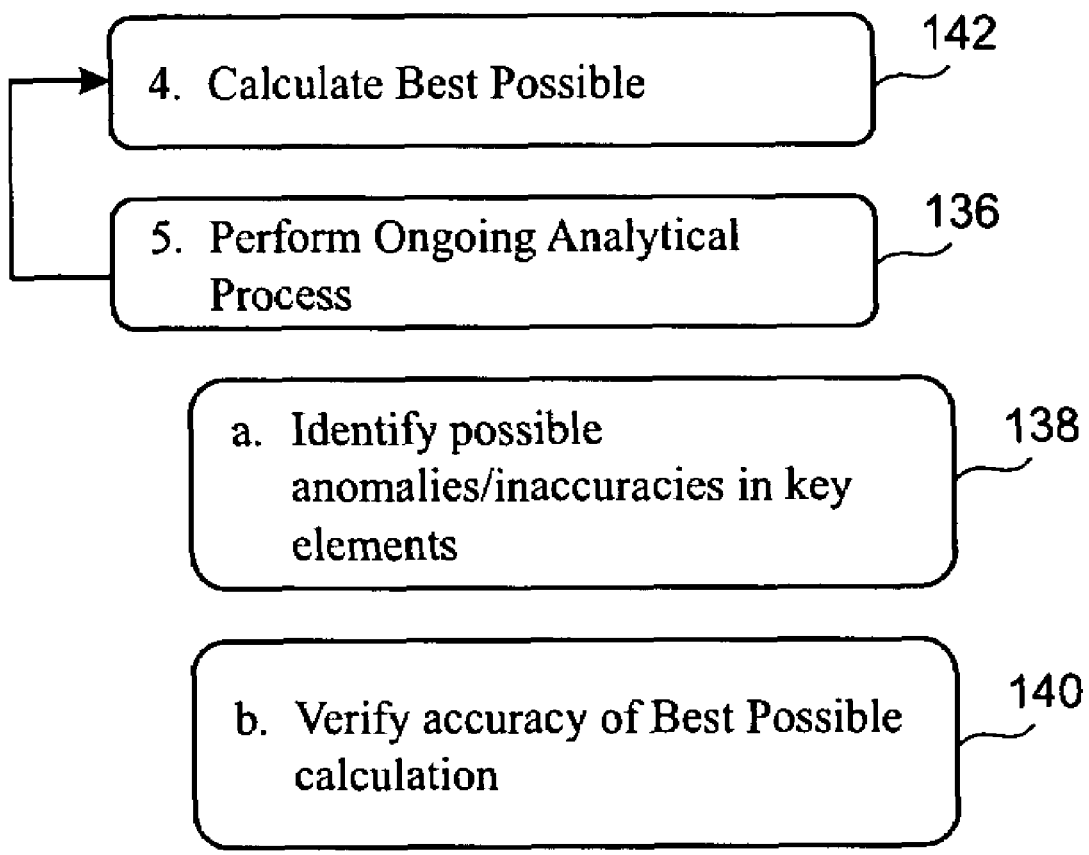

Referring to FIG. 3g, since contract terms may change and new contracts may be added over time, the system performs an on-going analysis, as indicated by the box 136. The on-going analysis is used to identify possible anomalies and/or inaccuracies in the system, as indicated by the box 138. The analysis can also be used to verify the accuracy of the best possible calculation, as indicated by the box 140. There are various analyses that can be performed. For example, the calculation for the best possible revenue for one or more selected accounts can be compared with the remittance advice messages included on a HIPAA 835 remittance form. Any discrepancies between the HIPAA 835 form and the best possible calculation for that patient account can be flagged for further investigation. For example, the contract terms may have been re-negotiated with the payer and the re-negotiated terms not modeled into the system. In this case, the new contract terms are modeled and mapped to various patient accounts. The best possible revenue is recalculated, as indicated by the box 142. There may be other anomalies, which can be corrected and the revenue calculation re-calculated.

Figure 3H:
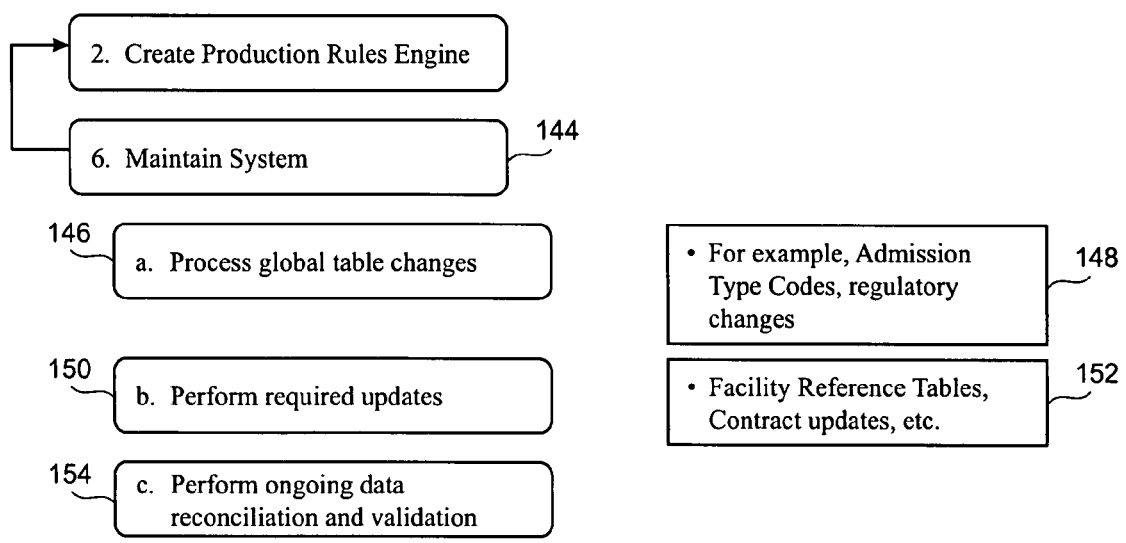

Referring to FIG. 3H, since other data used to calculate the best possible revenue periodically changes, the system is receptive to such changes as indicated by the box 38. For example, procedure codes periodically change, as mentioned above. These updated procedure codes as well as other data are uploaded into the system. For example, changes to the Global Tables are processed, as indicated by the box 146. These changes include regulatory changes, as indicated by the box 148. In order to keep up with changes in facility specific data, such data is updated, as indicated by the box 150. Facility specific data can include updating Facility Reference tables, contract updates, etc, as indicated by the box 152.

As indicated by the box 154, the system may perform ongoing data reconciliation by comparing data used by the system with data available from external sources. For example, the system may compare stored CPT4 Procedure Codes with the CPT4 Procedure Codes, available by the AMA, etc. Such on-going data reconciliation may be used to validate the data and the production rules engine used by the system to ensure the highest possible accuracy of the best possible calculations.

Figure 3I:
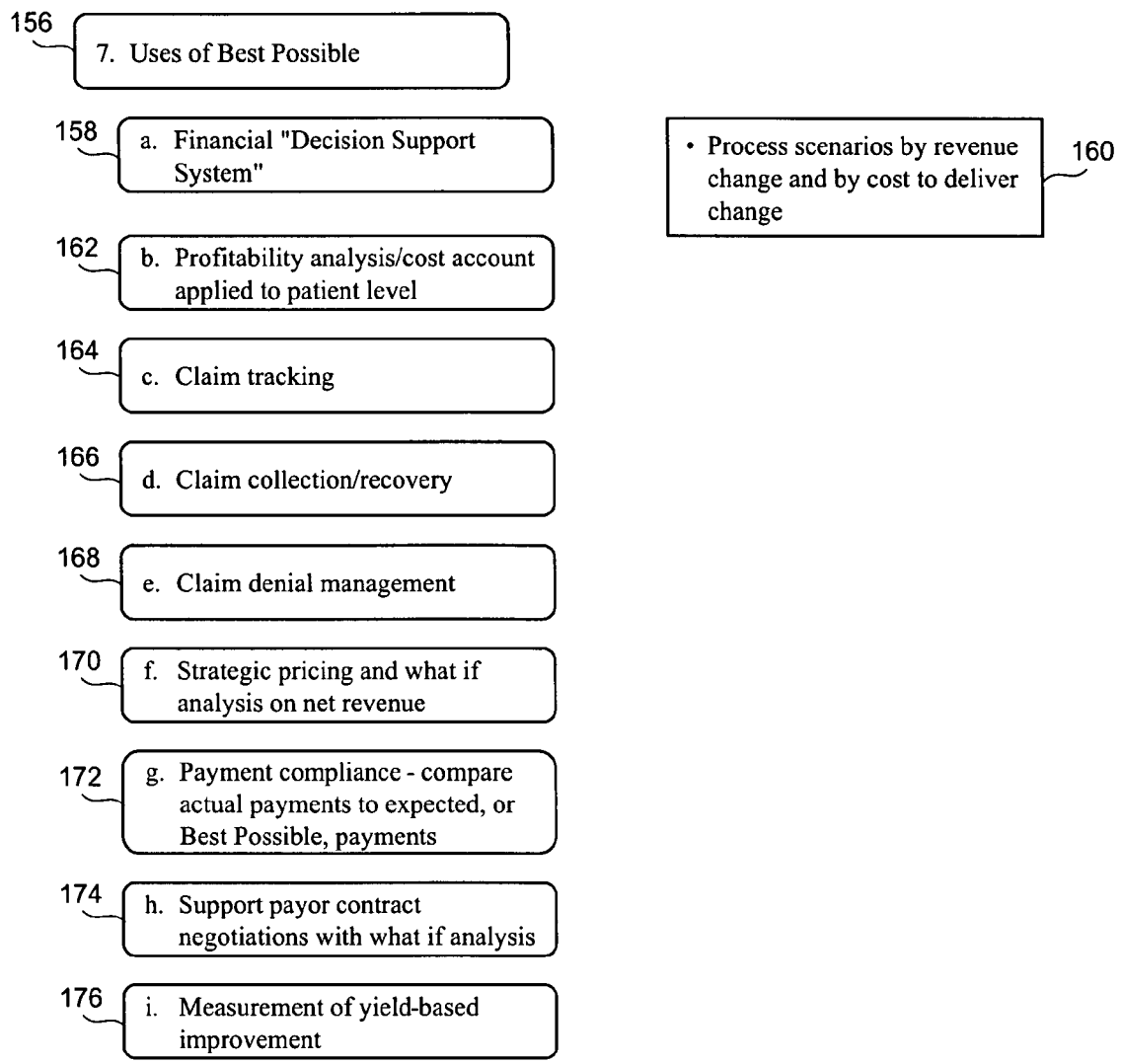

FIG. 3I illustrates exemplary uses of the calculation of the best possible revenue, as indicated by box 156. In particular, in addition to the Net Revenue Yield, discussed above, the best possible revenue calculation can be used for a multitude of other applications. For example, the best possible revenue calculation can be used for a "Decision Support System", as indicated by the box 158. The Decision Support System 158 can be used by management for various purposes. For example, the system can be used to process various scenarios, such as improved contract terms with payers and others, by revenue change and by cost before a change is actually implemented, as indicated by the box 160. Since the best possible revenue calculation is done on a patient account level, it can be integrated with profit and loss data and used for profitability analysis as a function of patient type, payer, etc., as indicated by the box 162. The calculation can also be used for various revenue management functions, including various revenue collection management functions, such as: claim tracking (box 164), claim collection/recovery (box 166), claim denial management (box 168), and payment compliance in which actual payments are compared to expected or best possible revenue (box 172).

Claim collection/revenue management relates to determining payment compliance of the individual payers, i.e. realization or actual yield as a function of the best possible revenue, as indicated in box 172. The actual yield is determined by simply dividing actual payments by the Best Possible revenue determination on an individual payer basis. More particularly, as discussed above, the best possible revenue is determined on an individual payer basis. As such, the actual yield can be determined for individual payers. Similarly, the impact on the total yield can be determined for each payer. As such, the healthcare provider can focus its collection efforts on the payers with the lowest yields, which will have the greatest impact on the overall yield.

The yield information can be used to determine individual payers with low actual yields. This information can be used for claim denial management, as indicated by the box 168, as well as payment compliance 172, as discussed above. In particular, the low yields can result from poor payer performance or claim denials. With respect to claim denials, claims are denied for various reasons, such as: lapse of coverage; medical condition not covered, incomplete medical documentation, authorization not received from insurance company prior to procedure or other upstream process failures.

Since the best possible revenue and the yield is determined on a patient visit level, the information can be used to more efficiently invoice the patients or other payers to increase the overall yield when claims are denied.

The yield information, as discussed above, can also be used in contract negotiations with payers, as indicated by box 174. Contract terms with payers can be negotiated by healthcare providers in terms of actual yield performance for the payer a given period of time. For example, the yield information can be used to negotiate better contract terms with payers with lower yields.

Yield data can also be used to determine the effectiveness (i.e. improvement of yield) of management decisions. In particular, the effect of adding and/or dropping certain private payers, such as a particular insurance company, can be measured in terms of yield improvement.

The best possible revenue calculation can also be used for various other strategic planning functions, such as: strategic pricing and "what if" analysis on net revenue (box 170). For example, the system for the best possible revenue and its applications, as discussed above, can be used to price the system to healthcare providers as a function of additional revenue that can be collected by a healthcare provider. Countless other uses of the best possible revenue calculation are possible.

Data Loader Logic Diagrams

FIG. 4 is a top level data flow diagram for a data loader for use with the system illustrated in FIG. 2. FIGS. 5A-5G are lower level logic diagrams for the data loader, i.e., rules engine, for use with the present invention. The data may include non-patient account specific data, such as updates of the Global Tables, Facility Specific Tables, etc., which is simply archived and used to update the various databases used by the system. Such data is only periodically updated in the system. On the other hand patient account data which includes total raw charge data 28 (FIG. 1), patient data 30 and payment data 32 is continuously updated in the system. All such data is continuously updated into the system to ensure that the calculation of the best possible revenue is as accurate as possible.

Figure 5A:
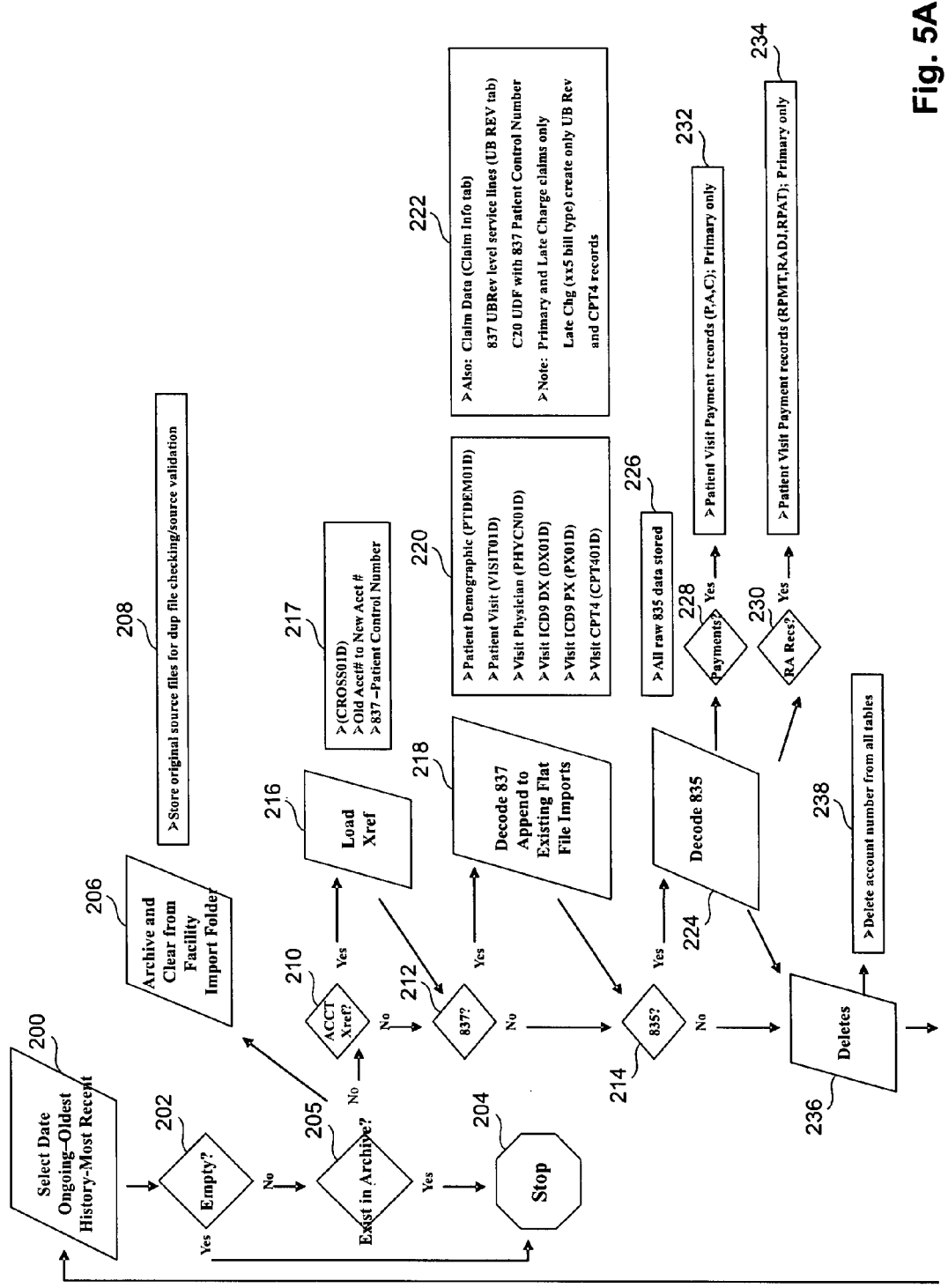
FIGS. 5A-5G are lower level logic diagrams for the data loader illustrated in FIG. 4.

Referring to FIG. 5A, all data to be imported into the system is imported into a Facilities Import Folder, whether it is non-patient account specific data or patient account specific data. Initially in step 200, the data is selected by date from the oldest history to the most recent. If the Facilities Import Folder is empty as determined in step 202, the system proceeds to step 204 and the data loading operation is terminated. The system continuously loops back and checks whether new data has been imported into the Facility Import Folder. Whenever, the system determines that new data has been uploaded to the Facility Import Folder, the system first checks whether the new data has already been archived in step 205. If so, the system proceeds to step 204 and terminates the data loading. If the new data is not in the archive, the system archives the new data and deletes the data from the Facility Import Folder in step 206. This allows the system to check for duplicate files and may be used for source validation, as indicated by the box 208. The data loader next ascertains the category of data to be loaded. In particular, the data loader checks whether the new data is an account cross reference in step 210; HIPAA 837, i.e., claim data, in step 212 or HIPAA 835, i.e., remittance data in step 214.

As mentioned above, all patient visits are assigned an account number. Thus, the data loader checks in step 210 whether there are any cross-references for the account number. As mentioned above, some healthcare providers assign new account numbers for every patient visit while others use the same account number for each patient irrespective of the visit. For those healthcare providers that assign individual account numbers for each visit, all previous account numbers are cross referenced to the new account number in step 216 by patient control number as extracted from HIPAA 837 forms, as indicated by the box 217.

If there no accounts to cross reference, the system checks in step 212, whether the data is HIPAA form 837 data. If so the HIPAA 837 data is decoded in step 218 and appended to the flat files, as discussed above. The HIPAA 837 data includes patient demographic data, and charge data including patient visit data, physician data, ICD9 DX data, ICD9 PX data and CPT4 data, as indicated by the box 220. The HIPAA 837 data may also include claim data, such as 837 UBRev level service lines and C20 UDF with 837 Patient Control Number, as well as late charge data, such as late charges per UBRev and CPT records, as indicated in box 222.

If the data is not cross reference data or HIPAA 837 data, the system checks in step 214, whether the new data is HIPAA 835 data, i.e., remittance data. If so, the 835 data from the HIPAA 835 form is decoded in step 224 and stored, as indicated by the box 226. The system then checks whether the HIPAA 835 data is payment data in step or a remittance advice in step 230. If the HIPAA 835 is payment data, the Patient Visit Payment records are updated with respect to payments, adjustments and co-insurance, as indicated by the box 232. If the HIPAA 835 data is simply a remittance advice, as determined in step 230, the Patient Visit Payment Records with respect to remittance payment (RPMT), remittance adjustment (RADJ) and remittance payment obligation (RPAT) are updated, as indicated by the box 234. Note, as shown, the Visit Payment records are indicated as being updated with respect to the primary insurance.

Deletion of account numbers are processed in step 236. The account numbers marked for deletion from the Delete Accounts list are deleted from all tables in step 238.

Figure 5B:
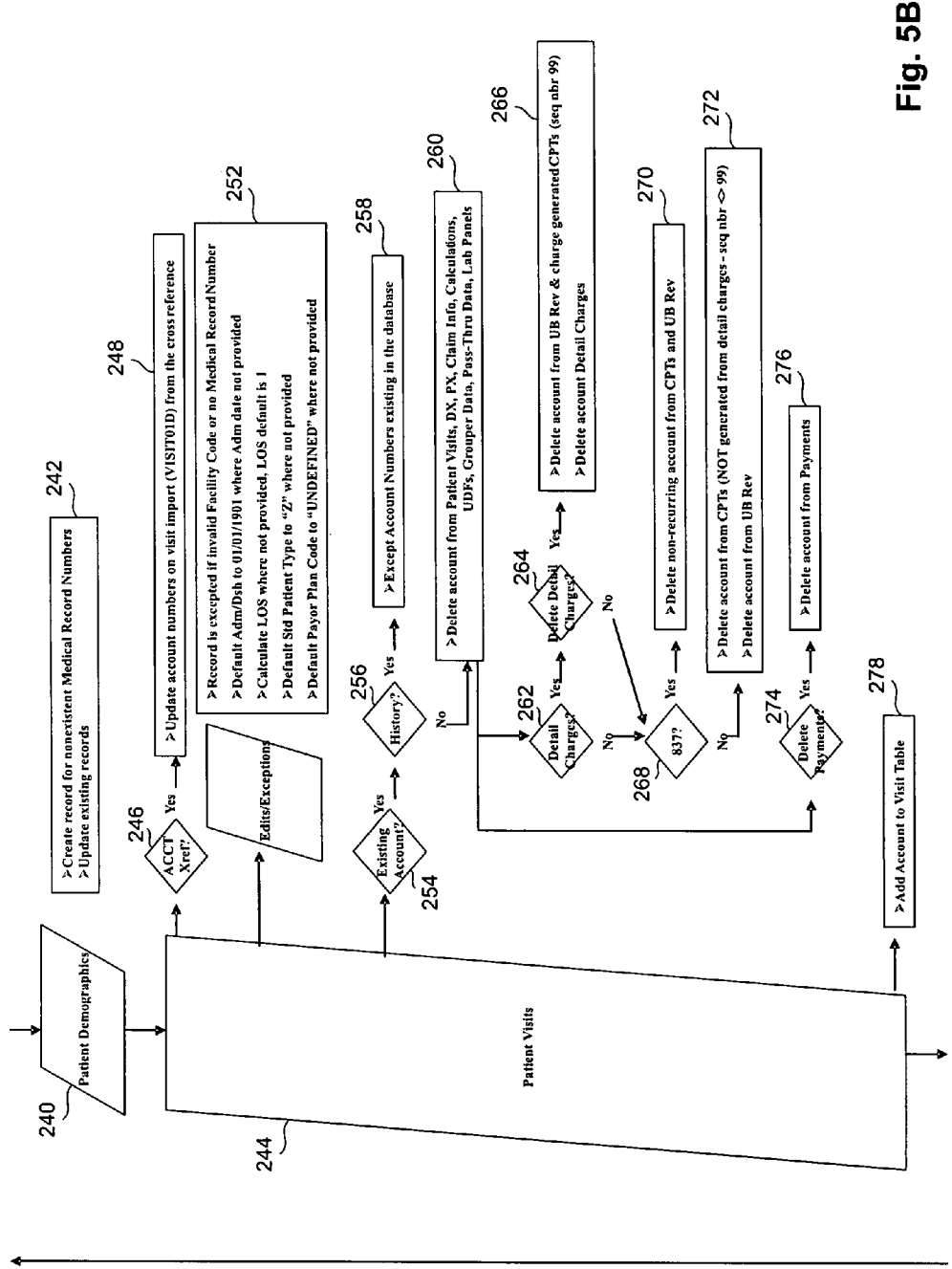

Turning to FIG. 5B, if the new data to be uploaded does not fall into the categories mentioned above, the system determines the data type and processes the data according to the rules established for uploading that data. For example, if the new data is patient demographic data, such data is used to update existing records in step 240. If the patient demographic data does not include a Medical Record Number, a record is created, as indicated by the box 242.

If the new data relates to patient visits, the system processes such data in step 244. If the data relates to account cross reference data, as determined in step, the account numbers on the visit import are updated from the cross reference, as indicated by the box 248. If the patient visit data is incomplete, it is treated as an edit/exception in step. The record is treated as an exception if the Facility Code is invalid or it does not include a Medical Record Number. Other examples of exceptions include: no admission date, no length of stay, missing patient type and no payer plan code. The remediation for each of these exceptions is identified in box 252.

First, the system checks in step 254 whether the data is duplicative of data already in the system by checking in step 254 whether the account number already exists in the system. If the patient visit data is determined to relate to an existing account in step 254, the system checks in step 256 whether the account number data was previously archived. If so, the account number is excepted, as indicated by box 258, and published on an error report for further investigation. If the account data was not previously archived, the new data is deleted from the system to avoid duplication. In particular, the account is deleted from Patient Visits, DX, PX, Claim Info, Calculations, UDFs, Grouper Data, Pass-Thru Data and Lab Panels, as indicated by the box 260. In addition, further deletions are required if the new data is already existing and relates to either Detail Charges, i.e., flat files, or 837 data. In particular, if the new data that is existing relates to flat files, i.e., selfpay patients, as determined in step 262, the system checks whether those flat files were deleted in step 264. If so, the system deletes the account from the UBRev and charge generated CPTs and deletes the account from the flat files, as indicated by the box 266. If the new data does not relate to flat files, the system checks whether the new data is HIPAA 837 data in step 268. If so the account is deleted from the CPTs and the UBRev tables, as indicated by the box 270. If the new data is neither flat file or 837 data, the account is deleted from the CPTs and the UBRev, as indicated by the box 272. The system also checks in step 274 whether the new data, that was previously determined to relate to an existing account, is payment data. If so, the account is deleted from the Payments table, as indicated by the box 276.

If the new Patient Visit data does not relate to an existing account, the data is assumed to relate to a new patient visit. In this case, the account number is added to the Patient Visit table, as indicated by the box 278. For new data that relates to Patient Visits, the data loader processes the data as a function of the sub-category of patient visit data. Exemplary sub-categories include various standard diagnostic, procedure and supply codes including: physicians, ICD9 DX, ICD9 PX, UBRev (837), CPT4 for insured patients, and Detailed Charges for selfpay patients, as well as payment data.

Figure 5C:
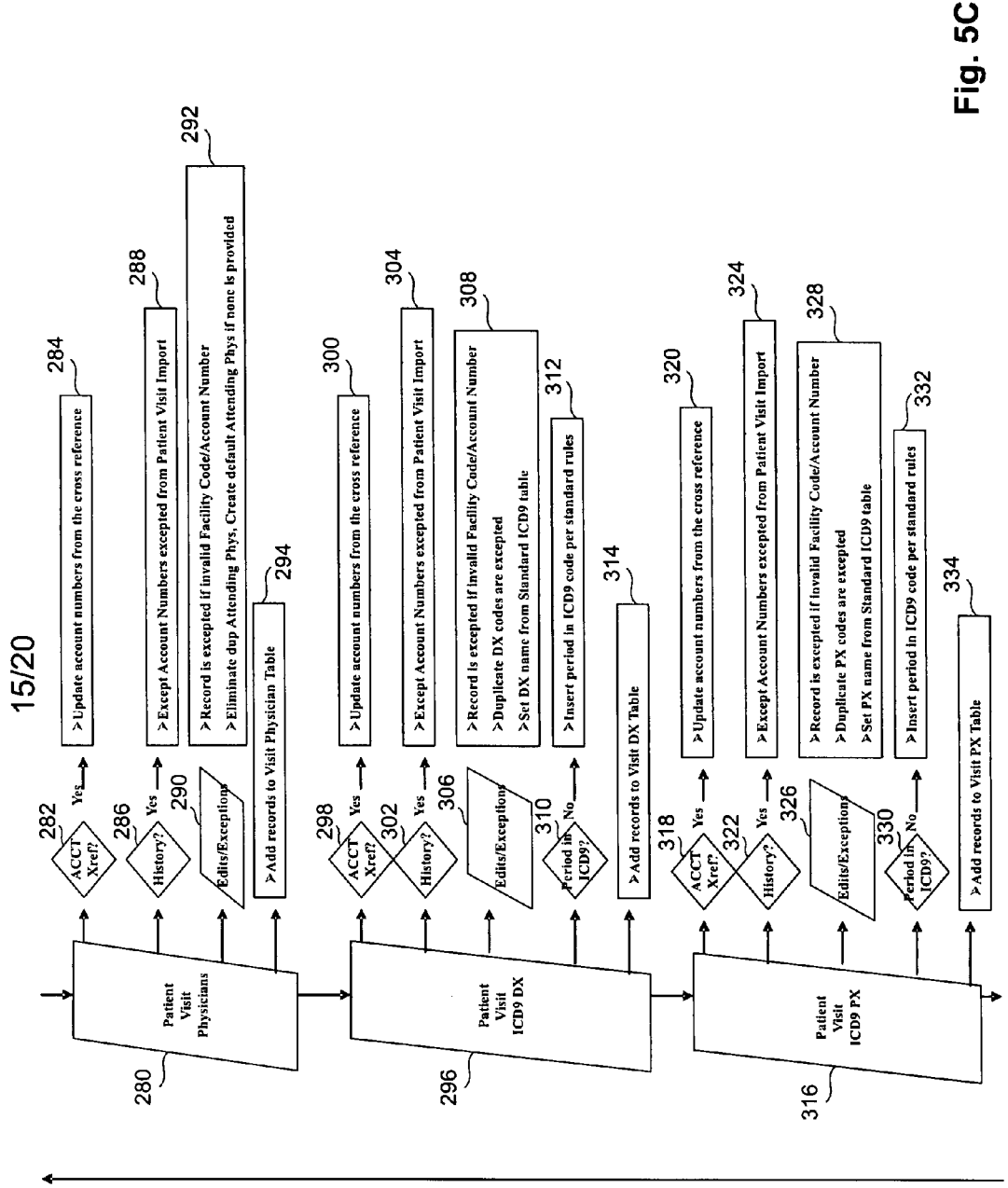

Referring to FIG. 5C, physician code is processed in step 280. The data loader, i.e., rules engine, first determines in step 282 whether the data is account cross-reference data. If so, account numbers are updated from the cross reference, as indicated by the box 284. If the data was previously archived, as determined in step 286, the account numbers are excepted and published on an exceptions report for further investigation, as indicated by the box 288. The data may also be excepted in step 290 if the data includes an invalid Facility Code or Account Number or if an attending physician is not provided, as indicated by the box 292. Alternatively, the data is added to the Visit Physicians table, as indicated by the box 294.

If the data is ICD9 DX data, it is processed in step 296. For ICD9 DX data, the system determines in step 298 whether the data relates to account cross-references. If so, the system updates the account numbers, as indicated by the box 300. If the data was previously archived, as determined in step 302, the account numbers are excepted and published on an exceptions report for further investigation, as indicated by the box 304. The data may also be excepted in step 306 if the data includes an invalid Facility Code or Account Number or if duplicate DX codes are listed, as indicated by the box 308. The system also checks in step 310 the format of the ICD9 DX code and specifically whether it includes a period. If not, a period is added to the end of the ICD9 DX code, as indicated by the 312. Alternatively, the data is added to the Visit DX table, as indicated by the box 314.

If the data is ICD9 PX data, it is processed in step 316. For ICD9 PX data, the system determines in step 318 whether the data relates to account cross-references. If so, the system updates the account numbers, as indicated by the box 320. If the data was previously archived, as determined in step 322, the account numbers are excepted and published on an exceptions report for further investigation, as indicated by the box 324. The data may also be excepted in step 326 if the data includes an invalid Facility Code or Account Number or if duplicate PX codes are listed, as indicated by the box 328. The system also checks in step 330 the format of the ICD9 PX code and specifically whether it includes a period. If not, a period is added to the end of the ICD9 PX code, as indicated by the 332. Alternatively, the data is added to the Visit PX table, as indicated by the box 334.

Figure 5D:
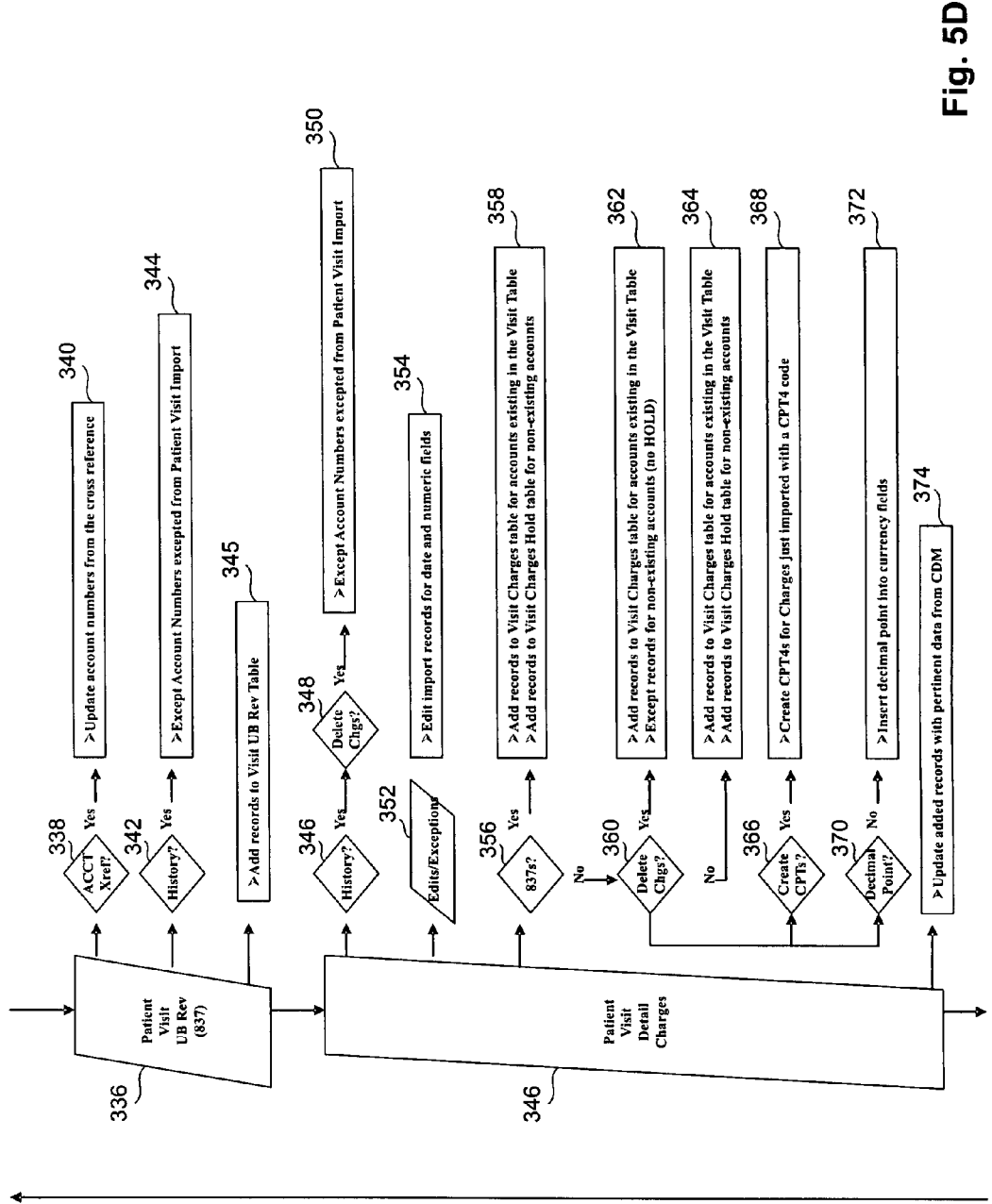

Referring to FIG. 5d, if the data is UBRev data, i.e., 837 data, it is processed in step 336. For UBRev data, the system determines in step 338 whether the data relates to account cross-references. If so, the system updates the account numbers, as indicated by the box 340. If the data was previously archived, as determined in step 342, the account numbers are excepted and published on an exceptions report for further investigation, as indicated by the box 344. Alternatively, the data is added to the Visit UBRev table, as indicated by the box 344.

If the data relates to Detail Charge data for selfpays, it is processed in step 346. For such data, the data loader determines if the data was previously archived in step 347. Next, the system determines in step 348 if the charges are to be deleted. If so, the account numbers are published as an exception on the Patient Visit Import file, as indicated by the box 350. Edits and exceptions of the Patient Visit Detail Charges are processed in step 352. These edits and exceptions are processed by editing the import records for date and numeric fields, as indicated by the box 354.

The rules engine is also able to process Detail Charges for which a HIPAA form 837 has been created in step 356. If a form 837 has been created, the records are added to the Visit Charges Table for accounts existing in the Visit Table or to a Visit Charges Hold table for non-existing accounts, as indicated by the box 358. If charges are to be deleted, as determined in step 360, the records are added to the Visit Charges Table for accounts existing in the Visit Table and the records are excepted and published on an error report for non-existing accounts, as indicated by the box 362. If the charges are not to be deleted, the records are added to the Visit Charges Table for accounts existing in the Visit table or added to the Visit Charges Hold table for non-existing accounts, as indicated by the box 364. In step 366, the rules engine decides whether to create a CPT. In particular, the rules engine creates CPT4s for any charges imported with a CPT4 code, as indicated by the box 368 if applicable. In step 370, the rules engine checks the format of the currency fields. If a decimal point does not exist, a decimal point is inserted into the currency field in step 372. Alternatively, the data is added to the Patient Visit Detail Charge Table with data from the CDM, as indicated by the box 374.

Figure 5E:
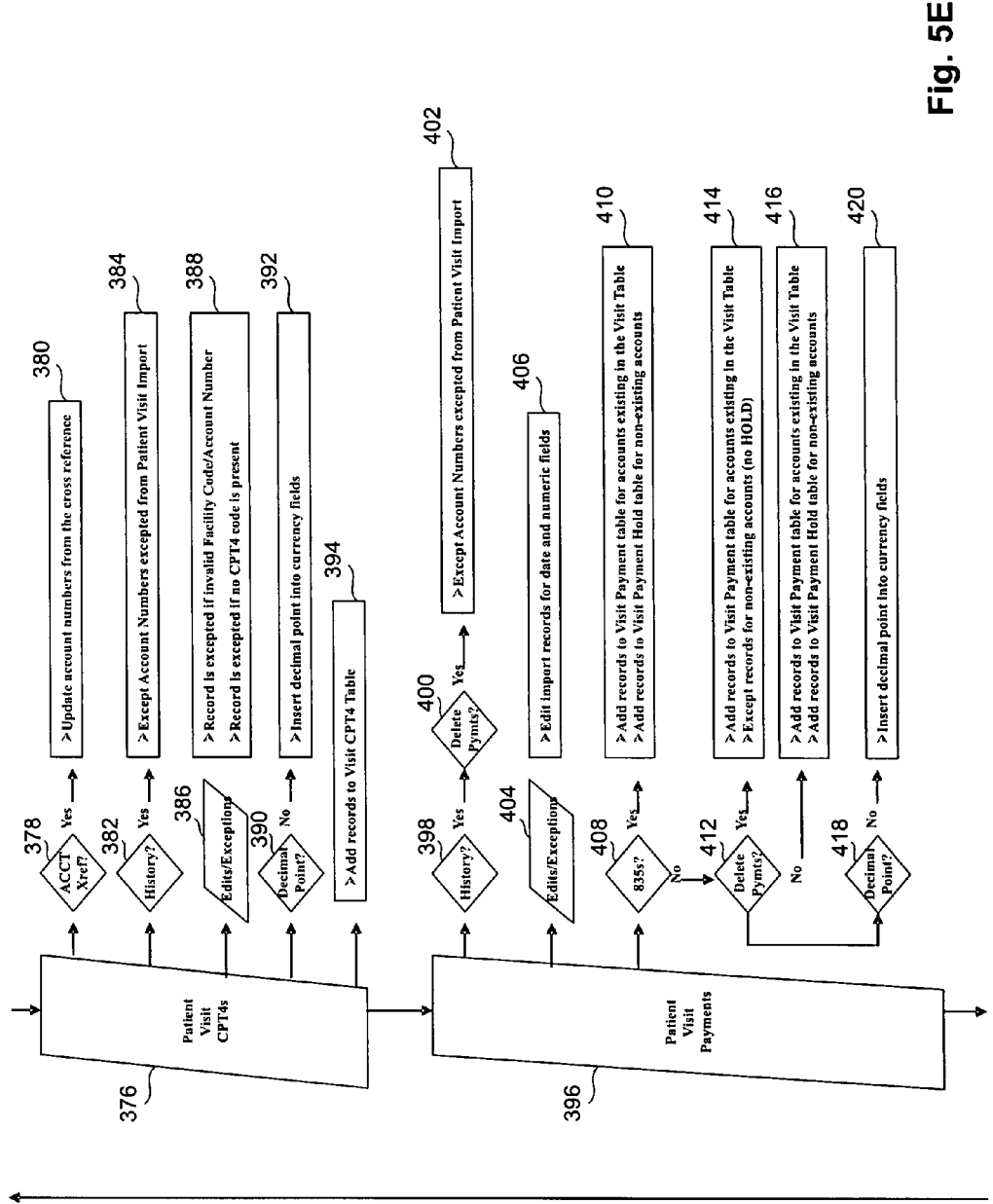

CPT4 data is processed in step 376 (FIG. 5E). For CPT4 data, the system determines in step 378 whether the data relates to account cross-references. If so, the system updates the account numbers, as indicated by the box 380. If the data was previously archived, as determined in step 382, the account numbers are excepted and published on an exceptions report for further investigation, as indicated by the box 384. The data may also be excepted in step 386 if the data includes an invalid Facility Code or Account Number or no CPT4 code is present, as indicated by the box 388. The system also checks in step 390 the format of the CPT4 code and specifically whether it includes a decimal point. If not, a decimal point is added to the currency field, as indicated by the 392. Alternatively, the data is added to the Visit CPT4 Table, as indicated by the box 394.

Payment data is processed in step 396. If the data was previously archived, as determined in step 398, the system next checks in step 400 whether payments are being deleted. If so the account numbers are excepted and published on an exceptions report for further investigation, as indicated by the box 402. Edits of the payment data are processed in step 404. In particular, import records are edited for date and numeric fields, as indicated by the box 406. Remittance data is initially processed in step 408. If the remittance data is a HIPAA 835 remittance form, the records are added to the Visit Payment Table for accounts existing in the Visits Table or to the Visit Payment Hold Table for non-existing accounts, as indicated by the box 410.

If the payment record is to be deleted, as determined in step 412, the record is added to the Visit Payment Table for accounts existing in the Visit Table and an exception is published for non-existing accounts, as indicated by the box 414. If the payment is not being deleted, the record is added to the Visit Table for accounts existing in the Visit Table and added to the Visit Payment Hold Table for non-existing accounts, as indicated by the box 416. The system also checks the format of the data in step 418 and adds a decimal point into the currency fields, if necessary, as indicated by the box 420.

Figure 5F:
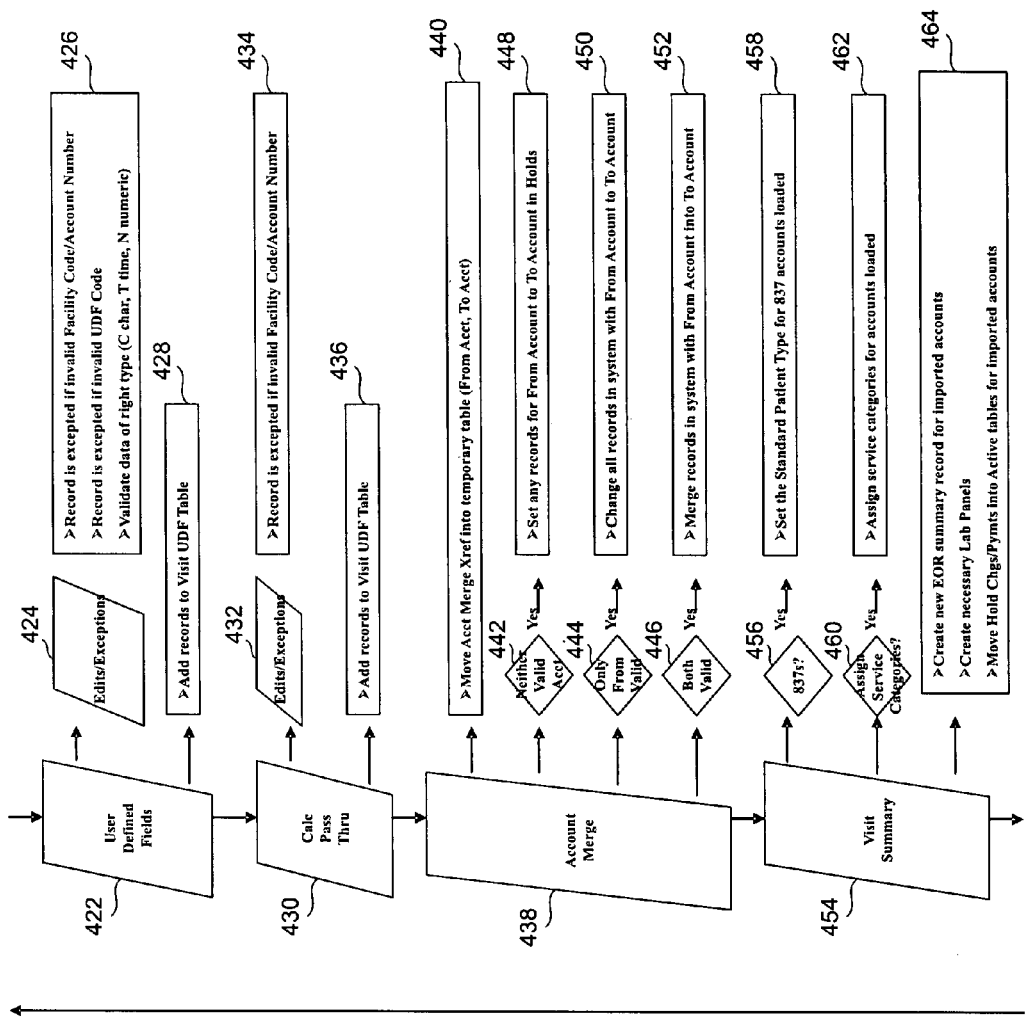
Figure 5G:
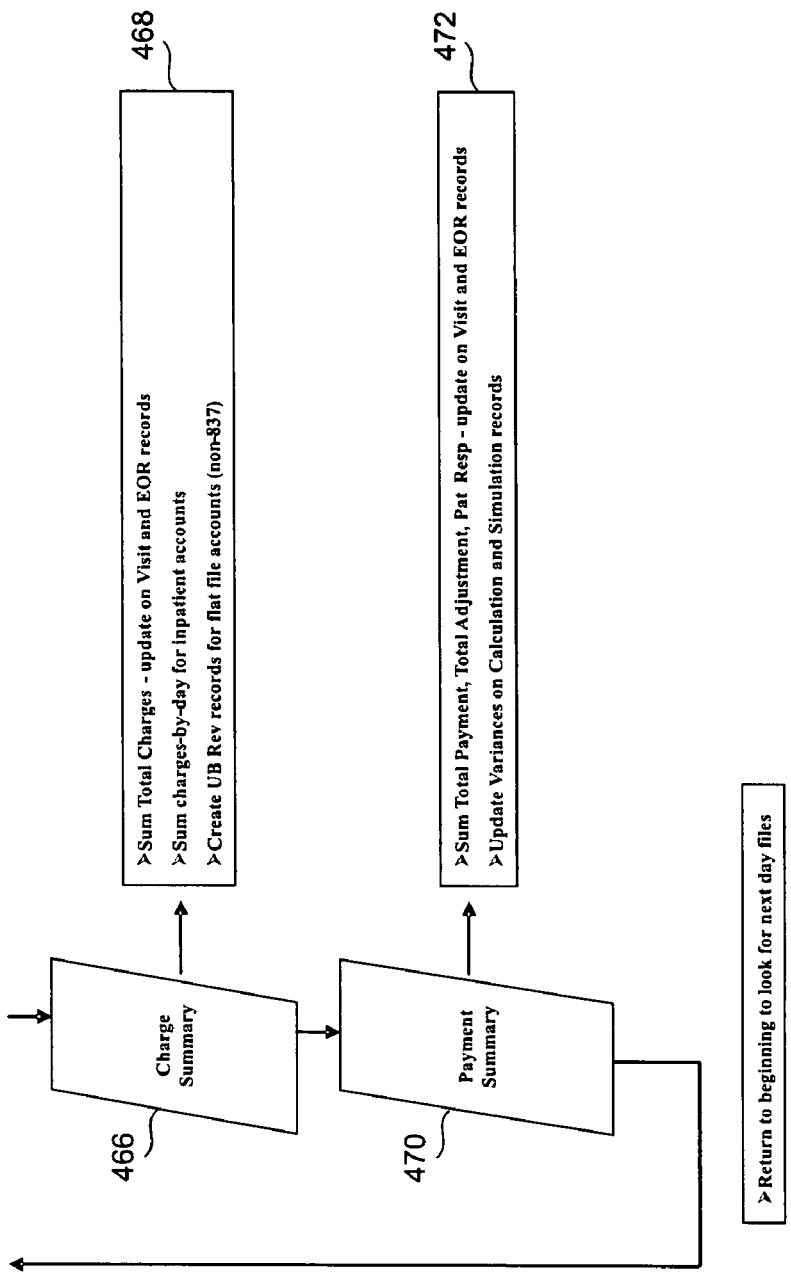

Referring to FIG. 5f, user defined fields are processed in step 422. Edits and exceptions of the user-defined fields are processed in step 424. The user defined field record is excepted if it contains an invalid Facility Code, invalid Account Number or an invalid UDF code, as indicated by the box 426. Additionally, the rules engine may verify that the user-defined data is of the right type, such as character, time or numeric data. User defined data is added to the Visit UDF Table, as indicated by the box 428.

Pass through charges are processed in step 430. Edits and exceptions of the pass thru charges are processed in step 432. The data is excepted and published on an error report if the record includes an invalid Facility Code or an Invalid Account Number, as indicated by the box 434. The pass thru data is added to the Visit UDF Table, as indicated by the box 436.

Certain providers merge accounts that were initially separate accounts. To ensure that only one visit survives from such merged accounts, initially separate accounts are combined into single accounts in step 438. In particular, cross-referenced account records are moved into a temporary table, as indicated by the box 440. The system checks in steps 442, 444 and 446 whether the existing account and the cross-referenced account are valid. If neither account is valid, the cross-referenced accounts, i.e., from the existing accounts, are sent to the "To Account Holds" table, as indicated by the box 448. All valid accounts are sent to the "To Accounts" table, as indicated by the boxes 450 and 452.

Visit Summaries are processed in step 454. For HIPAA 837 records, as determined in step 456, the Standard Patient Type for the 837 forms is loaded, as indicated by the box 458. If service categories are to be assigned, as determined in step, the service categories for the various accounts are loaded, as indicated by the box 462. As part of the Visit Summary processing, the rules engine creates new Explanation of Reimbursement (EOR) Summary Record for all accounts and creates any necessary lab panels, as indicated by the box 464. Also Hold Changes and Payments are moved into active accounts.

Referring to FIG. 5g, the Charge Summary Table is processed in step 466. This process includes summing of the total charges based upon updates of the Visit and EOR records; summing charges by day for inpatient accounts; and creating UBRev records for flat file accounts, as indicated by the box 468.

The Payment Summary is processed in step 470 and includes the Sum Total Payments, Total Adjustments and Patient Responsibility, that is updated based on Visit and EOR records. In addition, variances are also updated, as indicated by the box 472.

As mentioned above, data is continuously being input into the system. As such the data loader periodically loads the data. For example, the data may be loaded as mentioned above on a daily basis, as indicated in the box 474 and process the data, as mentioned above and repeat the data loading process the next day and continuously update the process on a daily basis.

Obviously, many modifications and variations of the present invention are possible in light of the above teachings. Thus, it is to be understood that, within the scope of the appended claims, the invention may be practiced otherwise than as specifically described above.

What is claimed and desired to be secured by a Letters Patent of the United States is:

1. A computerized method for calculating by way of a computerized processing engine under program control the best possible revenue a healthcare provider can lawfully expect at a given time, the method comprising the steps:
    (a) storing on a computer readable medium a plurality of contracts between a healthcare provider and a corresponding plurality of third party payers, each of which contracts identifies the amounts of payment that the corresponding third party payer will pay to the health care provider for medical services and supplies provided by said health care provider to patients covered by said corresponding third party payer;
    (b) storing on said computer readable medium patient data which (i) identifies the patients who have received the medical services and supplies provided by the health care provider, and (ii) identifies any of said plurality of third party payers which are obligated to pay at least a portion of medical expenses incurred by said patients who have received the medical services and supplies provided by the health care provider;
    (c) storing on said computer readable medium patient data which identifies the medical services and supplies provided by said health care provider to said patients who have received the medical services and supplies provided by the health care provider, to define raw charge data;
    (d) storing on said computer readable medium payments made to said health care provider by (i) said any of said plurality of third party payers which is obligated to pay at least a portion of medical expenses incurred by said patients who have received the medical services and supplies provided by the health care provider, and (ii) said patients who have received medical services and supplies provided by said health care provider; and
    (e) calculating, under program control by way of the computerized processing engine, the amounts of payment due to the health care provider at the given time by executing the following steps under program control:
        (i) determining whether any of the raw charge data incurred by said patients who have received medical services and supplies provided by said health care provider will at least be partially paid by said any of said plurality of third party payers which are obligated to pay at least a portion of medical expenses incurred by said patients who have received the medical services and supplies provided by the health care provider, by determining if said patients who have received the medical services and supplies provided by the health care provider are covered by at least one third party payer that has a contract with said health care provider;
        (ii) for patients who have received medical services and supplies, and for which at least a portion of said raw charge data are covered by the at least one third party payer that has a contract with said health care provider as determined in step (i), transforming said raw charge data to fees provided by the contract between said health care provider and said at least one third party payer, to define transformed fees; and
        (iii) calculating the amounts of payment due to said health care provider at the given time by summing raw charge data of patients not covered by a third party provider and said transformed fees and subtracting payments made by (i) said any of said plurality of third party payers which are obligated to pay at least a portion of medical expenses incurred by said patients who have received the medical services and supplies provided by the health care provider and (ii) said patients who have received medical services and supplies, to provide data representative of the total amounts of payment due and owing to said health care provider at the given time.

2. The computerized method as recited in claim 1, further including the step of dividing under program control payments received as determined in step (d) by data representative of said total amounts of payment due under program control to determine the yield in terms of said total amounts of payment due.

3. The computerized method as recited in claim 2, further including the step of determining under program control the yield for individual third party payers.

4. The computerized method as recited in claim 2, further including the step of determining under program control the profitability on a patient level based upon said yield data by analyzing the yield for one or more categories of medical services.

5. The computerized method as recited in claim 2, further including the step of determining under program control the yield for patients covered by third party payers and patients not covered by third party payers.

6. The computerized method as recited in claim 2, further including the step of determining under program control the yield for individual facilities of a health care provider.

* * * * *